(12) United States Patent
Zheng et al.

(10) Patent No.: US 8,753,847 B2
(45) Date of Patent: Jun. 17, 2014

(54) SELECTION AND ENRICHMENT OF PROTEINS USING IN VITRO COMPARTMENTALIZATION

(71) Applicant: New England Biolabs, Inc., Ipswich, MA (US)

(72) Inventors: Yu Zheng, Topsfield, MA (US); Richard J. Roberts, Wenham, MA (US)

(73) Assignee: New England Biolabs, Inc., Ipswich, MA (US)

( * ) Notice: Subject to any disclaimer, the term of this patent is extended or adjusted under 35 U.S.C. 154(b) by 0 days.

(21) Appl. No.: 13/966,018

(22) Filed: Aug. 13, 2013

(65) Prior Publication Data

US 2013/0331300 A1   Dec. 12, 2013

Related U.S. Application Data

(62) Division of application No. 13/415,504, filed on Mar. 8, 2012, now Pat. No. 8,551,734, which is a division of application No. 12/035,872, filed on Feb. 22, 2008, now Pat. No. 8,153,358.

(60) Provisional application No. 60/903,258, filed on Feb. 23, 2007.

(51) Int. Cl.
| | |
|---|---|
| C12P 19/34 | (2006.01) |
| C12P 21/06 | (2006.01) |
| C12N 9/00 | (2006.01) |
| C12N 9/12 | (2006.01) |
| C12N 9/14 | (2006.01) |
| C12N 9/16 | (2006.01) |
| C12N 15/00 | (2006.01) |
| C07H 21/00 | (2006.01) |
| C07H 21/04 | (2006.01) |
| G01N 33/573 | (2006.01) |

(52) U.S. Cl.
USPC ......... 435/91.5; 435/7.4; 435/69.1; 435/91.1; 435/91.52; 435/91.53; 435/183; 435/194; 435/195; 435/196; 435/320.1; 536/22.1; 536/23.1; 536/23.2; 536/24.1; 536/24.2

(58) Field of Classification Search
None
See application file for complete search history.

(56) References Cited

U.S. PATENT DOCUMENTS

| | | |
|---|---|---|
| 6,184,012 B1 | 2/2001 | Neri et al. |
| 6,489,103 B1 | 12/2002 | Griffiths et al. |
| 6,495,673 B1 | 12/2002 | Neri et al. |
| 7,138,233 B2 | 11/2006 | Griffiths et al. |
| 7,211,564 B2 | 5/2007 | Gorochov et al. |
| 7,252,943 B2 | 8/2007 | Griffiths et al. |
| 7,282,328 B2 | 10/2007 | Kong et al. |
| 2004/0209299 A1 | 10/2004 | Pinter et al. |
| 2005/0221339 A1 | 10/2005 | Griffiths et al. |
| 2006/0078893 A1 | 4/2006 | Griffiths et al. |
| 2006/0153924 A1 | 7/2006 | Griffiths et al. |
| 2006/0154298 A1 | 7/2006 | Griffiths et al. |
| 2006/0210982 A1 | 9/2006 | Yanagawa et al. |
| 2007/0077572 A1 | 4/2007 | Tawfik et al. |
| 2007/0092914 A1 | 4/2007 | Griffiths et al. |
| 2007/0184489 A1 | 8/2007 | Griffiths et al. |
| 2008/0004436 A1 | 1/2008 | Tawfik et al. |

FOREIGN PATENT DOCUMENTS

| | | |
|---|---|---|
| WO | 97/40141 | 10/1997 |
| WO | 02/22869 | 3/2002 |
| WO | 02/089498 | 11/2002 |
| WO | 2005/030957 | 4/2005 |
| WO | 2005/049787 | 6/2005 |
| WO | 2006/040551 | 4/2006 |
| WO | 2006/051552 | 5/2006 |

OTHER PUBLICATIONS

Bernath et al., "Directed Evolution of Protein Inhibitors of DNA-nucleases by in Vitro Compartmentalization (IVC) and Nano-droplet Delivery" 345 Journal of Molecular Biology 1015-1026 (2005).*
Williams et al., "Amplification of complex gene libraries by emulsion PCR" 3(7) Nature Methods 545-550 (2006).*
Smith, Science 228:1315-1317 (1985).
Hanes et al., National Academy Science 94:4937-4942 (1997).
Tawfik et al., Nat Biotechnol. 16:652-656 (1998).
Roberts et al. Proc Natl Acad Sci USA 94:12297-12302 (1997).
Doi et al. Nucleic Acids Res 32:e95 (2004).
Ash, M. and Ash, I. Handbook of industrial surfactants. Gower Publishing Ltd: Aldershot, Hampshire, UK (1993).
Schick, Nonionic surfactants. Marcel Dekker: N.Y. (1996).
Saiki et al., Science 239:487-91 (1988).
Cahill et al. Clin. Chem. 37:1482-5 (1991).
Chetverin et al. Progress Nucleic Acid research Mol. Biol. 51, 225-70 (1995).
Katanaev et al. Febs Lett 359:89-92 (1995).
Landegren et al., Science 241:1077-80 (1988).
Barany PCR Methods Applic. 1:5-16 (1991).
Fahy et al., PCR Methods Appl 1:25-33 (1991).
Walker et al., Nucleic Acid Research 20:1691-6 (1992).
Zheng et al. Nucleic Acid Research 35:e83 (2007).
Ghadessy, et al., Prot. Eng. Des. Sel., 17(3):201-204 (2004).

* cited by examiner

Primary Examiner — Jennifer Dunston
Assistant Examiner — Nancy J Leith
(74) Attorney, Agent, or Firm — New England Biolabs, Inc; Harriet M. Strimpel

(57) ABSTRACT

Compositions and methods are provided for selection and enrichment of a target gene from a library of polynucleotide sequences such as might be formed from a genome or by random mutagenesis of a genetic sequence. The selection and enrichment occurs in aqueous droplets formed in an emulsion that compartmentalize individual polynucleotides from the library or a plurality of polynucleotides that may include polynucleotides not derived from the library, transcription and translation reagents and optionally additional chemical and enzyme reagents. The selection and enrichment method utilizes a polynucleotide adaptor which when ligated to the polynucleotide fragment enables amplification to occur in the presence of an adaptor specific primer.

3 Claims, 6 Drawing Sheets

Figure 7 (SEQ ID NO: 5)

```
gcgcctggcggagctggtgagggaggaggcggggggaccttcaggaggctcccgccccagggaggagaggcccggggagg
cccctcacgggggggggcctcgagggctccccgccgggcgagggccaagcggagcgcccctcccccctacctcacctac
gtccgcaaggagtgccgcctccgccccgaccagctggacgccctcaccgcctggccgggagaggaaggggaaggggggaa
aggatcacggagaacaccctcatccgctgggcggtggacttacttttgaaaaaactagagctggaaacggggagcgacgg
aaaggaggtgacatgacgcggatgttcgagacgcttgcagaacttgagcacgcttttcaaaacttgcgcgaacaacttgg
cgcaatggtaacggcgaatgaagacttttccccttttggtcgtcgacctttttccggagccggcggcatgtcctacggct
tcaaatattggggggataggctttacaaaataatcggtgcggtggatctcgaggtggccaaacccagcgacagcaaggca
aaaaagggcggcggggaacgaactgcaacgccacatacgaggccaatatcggcatacgcccgttaaaagccgatataac
ggaacttaatccccgtgaatacagagaaaatttgggtcttgaagtgggtcagttaggcgtacttatttcctgcgcccct
gcacgggattcagtcaaaaaaactttctgaaccaccagaacgatgacccacgaaaccacttggtgaggagaagcggggtt
tttttggaggaattttttaccagagttcttcgtgatggaaaacgtcccagaaatgatgttgggaaaacaccgtcaccattt
tgaagaactgaaggagatactcgtaggtttgggttattcctacaccgccggcgtgttggatttctccactctaggtttgc
cgcaacgaagaaagcgtgccgtggttatggcctggcgggaaggtagacgaatcccggctctacctcgctttttctcttcc
cctcctacggtacgggaggcaatcggccatcttccacctctctccgccggagaaacacatccaaacgatccgatgcacag
atgtccaaggcacaccccggaggtcatgaaagaattaaggccgtacccagggacggaggttcctggatcgacttggcct
ccagaaatccggaactccttattccctcgatgaaaaggaaactacgggaaggaaagaagggtctttttcccgacgtctac
ggacggatgtcctggaattccccgcgcctacgatcacgagggaatgcggccaccccggcaacggacgctacctacaccc
cgaacaggacaggatgttatctataagggagatggctatattacaaggttttcctcccaattacacctttattggaaacc
tcaaccaatgctacaaccaaatcggagacgcggttccccccctggttctcgcacgattgcgggcctcttttctcctcctg
aagctcgggctgaactggggccaagtcatgaaccgccatatacatgtctccaatctcaattggctttatttcgaagagca
cgtcccgagagcgcaggtggaacaggatcctctcctaatacccctaagccggttgccgtacatctagaggaggaaaacgat
gatcccggaacacggaaacagaagcgacgaaacaatcaaggaattaatcgcccgccttccctgggcaccgaaagcttgg
atacgctagagagcgagaaagaagaagcaaaaaaaatcgatttgctttcgagaacacatagaggtgcggaaatgatacgt
tacgttctaacacacatggagtccatcttcaaaaaatcgttctctgaggagactacctccccccctagcctcggcacttt
ccgcttctttcctcagcatgaacaagaaggccaaaagcttataaagcatcttttacaacaaggcataaaccccgcaaattc
ttttcgtagaaagtagttccgattttgagaaaaacaataaaagcaagtttacacgcaggcataaccaaaaaactcatc
aacaactaccgcacgacggacagcgatcagctcaaacagtggatcaactcggcaatactcctcgccttccggacctacgt
tgatttgactgggaggaaaaccttccaagaaagctggccagagtgcgtaaccaaagaagacgtctcaaaattcttggagt
ttaccgcaacgatgaacttgggagtcatggcggacggctggtggagaaaccaggtaggtgagaaagctgtgcaacttttc
ataaatgaaatcgagaaggcgttgaagaagctttattcaaaaaaatcctatcgttttgagcctaacgaggacagcccgag
cgtccgcgaatacatcgtaaccaacaccaccaacgaaacgcaactgatttttcgattcggagaaccagattttctgtaa
aaatccgcaacgaaaaaatggaaaaaatactcatttttaggcgaaatagggggcgctttgacaaatcgaacctacaagag
agctggtacacaaccatccaaaataggatgggaagggcaggaaacgaggggcaaaaacgcggccagtgtttttgttcttgt
tcaaaattactttgtgaaggaagaaaagaaacaaataaatgatctttgaacgaaagtgaaaaaaagggcctcaagttgg
gtcttttcagcttggccaagttgatgttctctcaagaggagaggcgaagatttgaagaatgcatcaaaggcctgatcgac
cttctagagctccgataaccctggcaacagcttcctgcggcgccttttcaattcatgttcccaaatccttacgaccgac
caccctgtctgccaggagttcatcaactcgtgcatcgcgttgcctgttctcttttatcttcctcctccaaaactccgc
attcgtcttaggtttcttattacagacggggcaaccgtgccagaaacatccgtcgacaaaaatcgccactttccgtttgg
gaaatacgacatccggtcgcccaggaaggttgttttttatacggtagcccccttataccggcaaccgccaagagacgacgc
aactttacttccggtcccgtggaggaagtctttactttcctcatcaactcagatcttttctccggagtaaaaatatccat
aaaaacccgtgtcgaaatcggctcggcttaatcctagacaagcacttccggcagcgcccgggcggcctcc
```

SELECTION AND ENRICHMENT OF PROTEINS USING IN VITRO COMPARTMENTALIZATION

CROSS REFERENCE

This application is a divisional of U.S. application Ser. No. 13/415,504, filed on Mar. 8, 2012 which is a divisional of U.S. application Ser. No. 12/035,872 filed Feb. 22, 2008 which claims priority from U.S. provisional application No. 60/903,258 filed on Feb. 23, 2007, herein incorporated by reference.

BACKGROUND OF THE INVENTION

Darwinian evolution generates diversity and allows improvement of an individual's component parts in a changing environment. One approach to designing enzymes with altered specificities is to utilize evolution in a context that can be managed in vitro. This kind of approach requires a linkage between genotype and phenotype and a strategy for selection and enrichment of distinct genotypes. Methods based on these considerations, include phage display (see for example Smith, *Science* 228:1315-1317 (1985), and U.S. Pat. No. 7,211,564); mRNA display (Hanes et al., *Proc. National Academy Science* 94:4937-4942 (1997), and Tawfik et al., *Nat Biotechnol.* 16:652-656 (1998)); and ribosomal display (Roberts et al. *Proc Natl Acad Sci USA* 94:12297-12302 (1997)). These methods utilize display of a desired phenotype on the surface of a particle that is capable of replication.

An alternative method of directed evolution that has been referred to as in vitro compartmentalization (IVC) relies on forming an emulsion of aqueous droplets in oil where the aqueous droplets contain a controlled amount and type of polynucleotide together with, at a minimum, a transcription and translation system to permit expression of any genes encoded by the encapsulated polynucleotides. The water droplets in these emulsions are also referred to as microcapsules in at least some of the publications listed below. The protein product of transcription and translation can then be detected by some form of assay that preferably permits enrichment of the target gene which may be initially present at an amount as low as 1 in $10^{10}$ droplets (see for example, Doi et al. Nucleic Acids Res 32:e95 (2004), U.S. Pat. Nos. 6,184,012, 6,489,103, 6,495,673, 7,138,233, and 7,252,943, U.S. Publication Nos. 2005/0221339, 2006/0153924, 2006/0154298, 2006/0078893, 2007/0077572, 2007/0092914, 2007/0184489, and 2008/0004436, and International Application Nos. WO 2006/040551 and WO 2006/051552).

If the problem of selection and enrichment can be solved, the ability to stably create as many as $10^9$-$10^{10}$ individual aqueous droplets in a single emulsion where each droplet contains a different molecule from a library of molecules could provide a rapid screening method for target genes encoding a desired phenotype in an extensive sequence space.

Unfortunately, reported screening and enrichment methods using IVC have been disappointing. For example, Doi et al. described a screening method for selecting and enriching for a genotype expressing a restriction endonuclease phenotype. Doi et al. used a DNA polymerase to incorporate dUTP-biotin to the sticky ends generated by restriction endonuclease cleavage permitting strepavidin affinity purification. Only 10-fold enrichment of a single polynucleotide was achieved in one round of in vitro compartmentalization. Consequently, a large number of rounds of enrichment were required to select an active phenotype, FokI, from a randomized FokI library.

In vitro compartmentalization using emulsions offers a potentially powerful method of directed evolution if selection of a protein activity and its enrichment in a solution can be optimized to allow efficient recovery of a target gene from the extensive sequence space.

SUMMARY

In an embodiment of the invention, a method is described for selection and enrichment of a target gene, wherein the method includes providing a library of polynucleotide fragments in which one or more polynucleotide fragments comprise a target gene encoding a protein with a desired activity. The polynucleotides in the library are encapsulated in a plurality of aqueous droplets in an emulsion, wherein each of the aqueous droplets in the plurality of droplets contains (i) a mixture of enzymes with transcription and translation activity, and (ii) one or more polynucleotide fragments from the library of polynucleotide fragments. The target gene from the library is transcribed and translated to provide a protein that has an activity that permits the polynucleotide fragment to become covalently linked to a polynucleotide adaptor in a reaction catalyzed by a ligase. Whereas ligation preferably occurs between complementary sticky ends on the polynucleotide fragment and the polynucleotide adaptor, in an embodiment of the invention, ligation may also be achieved through blunt-end ligation provided that the blunt end on the polynucleotide fragment is ligatable. This can for example be achieved through the activity of a restriction endonuclease. In either case, the target gene can then be selectively amplified using an adaptor-specific primer. The adaptor-specific primer preferably has a sequence that is present in the adaptor only and not in the polynucleotide fragment. However, the primer may have a sequence that is in large part located in the adaptor but overlaps with a short sequence (for example, less than 20 nucleotides) at the terminus of the polynucleotide fragment. Examples of target genes include those that encode proteins with activities selected from the group consisting of: ligase activity such as RNA or DNA ligase activity; polynucleotide cleavage activity such as restriction endonuclease activity, nicking endonuclease activity or homing endonuclease activity; transcription or translation activity such as tRNA synthetase activity or RNA polymerase activity; and reverse transcription activity.

In a further embodiment, a second primer is utilized in polymerase-dependent amplification that may hybridize to a sequence common in all the polynucleotide fragments in the library where the sequence is located at the opposite end of the polynucleotide from the adaptor-ligated end. Preferably, the specific sequence is also external to the gene.

In one embodiment, the aqueous droplets are disrupted after transcription and translation of the target gene and before ligation of the adaptor to the polynucleotide fragment. In another embodiment, the aqueous droplets may be disrupted after ligation and before amplifying the gene.

In one embodiment, certain aqueous droplets may include a plurality of polynucleotide fragments wherein the plurality of fragments further includes a plurality of genes. In another embodiment, each of the aqueous droplets described above may further contain one or more of a second polynucleotide fragment, not from the library, containing a gene encoding a defined second protein. In one example, the gene encoding the defined second protein has polynucleotide cleavage activity. In another embodiment, each of the aqueous droplets described above contains a reagent enzyme with polymerase-cleavage activity.

Once the target gene is amplified, an additional round or rounds of selection and enrichment may be desirable, in which case, the product of amplification is encapsulated in a plurality of aqueous droplets in an emulsion in the presence of a mixture of enzymes for transcribing and translating the gene, allowing the target gene to be expressed and permitting ligation to a second or additional polynucleotide adaptor and amplifying the target gene using a primer specific for the second adaptor. The adaptor used in each round preferably differs from the adaptor in the previous round. However, in another embodiment, the adaptor may be reused provided that it is removed from the amplified target gene prior to the next round of encapsulation.

In a further embodiment of the invention, enrichment of the target gene after one round of selection may be at least 50-fold, 70-fold or 100-fold.

In a further embodiment, individual polynucleotide fragments in the library contain a recognition sequence for at least one of a restriction endonuclease and a nicking endonuclease in a region of the fragment outside the gene sequence.

In a further embodiment, a sticky end is formed on the polynucleotide fragment by cleaving the polynucleotide fragment with the protein expressed by the target gene optionally in combination with a second enzyme activity provided by an enzyme reagent or by a protein encoded by a second polynucleotide fragment. In the latter case, the expression and/or activity of the protein encoded by a gene on the second polynucleotide may depend on the protein expressed by the target gene.

For example, where the protein expressed by the target gene has tRNA synthetase activity, this activity enables a restriction endonuclease encoded by a gene on the second polynucleotide fragment to be transcribed and translated and to cleave the polynucleotide fragment containing the target tRNA synthetase gene to generate a sticky end for ligating to an adaptor thus causing selection and enrichment of the target gene.

In another example, the protein expressed by the target gene is a restriction endonuclease that cleaves DNA to form a blunt end on the polynucleotide fragment. Optionally, a second enzyme activity is provided to convert the blunt end to a sticky end where the second enzyme activity may be a nicking endonuclease. An adaptor with a compatible sticky end can then be ligated to the polynucleotide fragment containing the target gene. In another example, the protein expressed by the target gene has nicking endonuclease activity, and the second enzyme activity is a restriction endonuclease activity. The activity of the two enzymes results in creation of a sticky end on the polynucleotide for ligation to an adaptor and subsequent amplification.

In a further embodiment, the library of polynucleotide fragments contains genomic DNA (gDNA). In an example, the target gene is a naturally occurring gene, where the method additionally includes cloning the naturally occurring target gene from the amplified DNA thereby providing a means for readily obtaining new naturally occurring genes from the environment with targeted functionalities.

In a further embodiment of the invention, the target gene is a mutagenized gene having a desired cleavage, synthetic or ligation protein activity.

Examples of target genes from genomic libraries or mutagenized libraries include those encoding proteins with an activity selected from ligase activity such as RNA or DNA ligase activity; polynucleotide-cleavage activity such as restriction endonuclease activity, nicking endonuclease activity or homing endonuclease activity; transcription or translation activity such as tRNA synthetase activity or RNA polymerase activity; and reverse transcription activity Examples of activities that may be selected for include a change in a desired specificity from that found in a naturally occurring protein. In one embodiment, a change in cleavage-site specificity for a restriction endonuclease may be sought. In this example, the desired unnatural cleavage site would be introduced at or near the terminus of the polynucleotide fragment in the library so that a target gene would be selected and enriched only if the encoded protein cleaved at the desired unnatural site to generate a sticky end for ligation to an adaptor. Another example includes selecting and enriching for an enhanced polynucleotide cleavage activity. Alternatively, a target gene may be selected and enriched for on account of the ability of the encoded protein to cleave a DNA sequence at an unnatural distance from its recognition site compared with a wild-type protein.

Other examples include screening libraries of mutagenized polynucleotide fragments for a target gene-encoding a protein with novel ligase activities such as altered temperature optima for ligation, or altered cofactor requirements.

These above examples are not intended to be limiting for the use of the embodiments of the method.

Embodiments of the invention have been exemplified by the cloning from nature of a novel restriction endonuclease, here named TspMI. Additional embodiments of the invention further include a vector containing the gene encoding TspMI and a host cell transformed with the vector.

In an embodiment of the invention, a composition is provided where the composition is an emulsion of a hydrophilic solution in a hydrophobic liquid, the hydrophilic solution forming a plurality of droplets, each of the droplets containing: (i) a mixture of enzymes with transcription and translation activity; and (ii) a polynucleotide fragment from a library of polynucleotide fragments, the polynucleotide fragment having a sticky end or a recognition site for an enzyme capable of cleaving the polynucleotide to create a sticky end. The droplets in the emulsion may further include a polynucleotide adaptor with a sticky end, the sticky end being complementary to the sticky end created or present on the polynucleotide fragment. The droplets in the emulsion may further include a restriction endonuclease reagent. The droplets in the emulsion may include a plurality of polynucleotide fragments, wherein one of the polynucleotide fragments encodes a restriction endonuclease reagent.

A library of DNA fragments together with transcription and translation reagents are dispersed into aqueous droplets in an emulsion (1). If an active restriction endonuclease is expressed in vitro in the droplets, cleavage of the terminus of the DNA fragment containing the encoding gene occurs at the endonuclease recognition sequence on the polynucleotide fragments to generate a sticky end. This is denoted by —X. The reaction in the emulsion is quenched by, for example, heating and/or adding EDTA. The emulsion is broken by adding water-saturated ether. DNA fragments are recovered from the aqueous phase (2). An excess of double-stranded DNA adaptor fragments with compatible sticky ends (X—) are added to the DNA fragments. Ligation occurs only between the recovered DNA fragment with a sticky end and an adaptor with a compatible sticky end (—X—) (3). Adaptor-specific PCR amplification is performed after which purified amplified DNA either enters the next round of selection or is cloned (4).

Figure 1A:
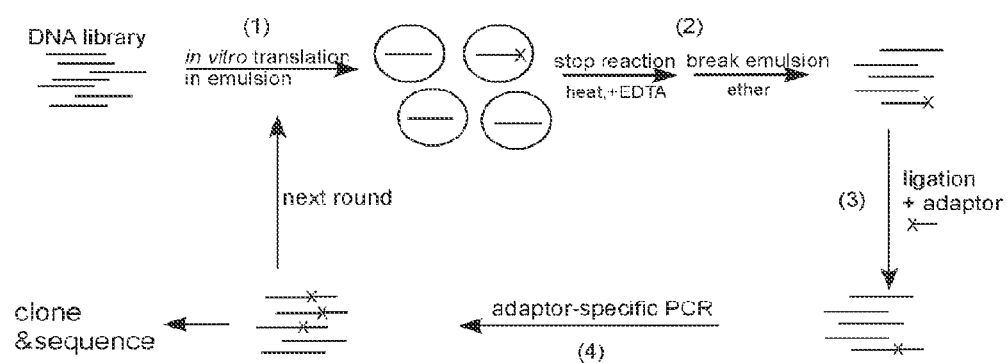
FIG. 1A shows a diagram of the in vitro selection and enrichment of a target gene encoding a restriction endonuclease.
Figure 1B:
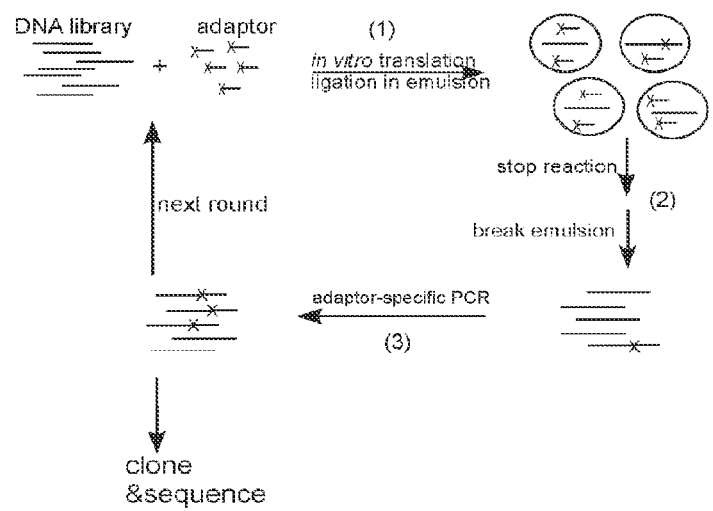

FIG. 1B shows selection of a target gene that encodes a protein with ligase activity.

A library of DNA fragments together with transcription and translation reagents and polynucleotide adaptors are dispersed into aqueous droplets in an emulsion. Ligation occurs in individual droplets that contain DNA fragments that encode the ligase activity (—X—). Ligation does not occur inside those droplets where there is no ligase-encoding genes (1). After an effective time period for transcription and translation, the reaction is stopped and the emulsion broken. DNA polynucleotides are recovered from the emulsion (2). Adaptor-specific PCR amplification is performed after which the recovered amplified DNA either enters the next round of selection or is cloned (3).

Figure 1C:
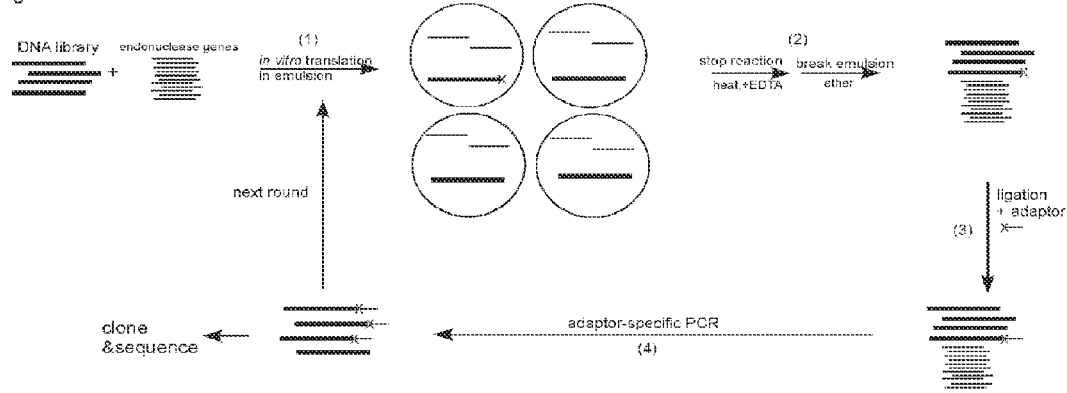

FIG. 1C shows coupled selection of an enzyme. A library of polynucleotides, adaptors, in vitro transcription and translation reagents minus a particular tRNA synthetase and a second polynucleotide fragment encoding a restriction endonuclease are emulsified into aqueous droplets. If a target gene encoding protein with the particular tRNA synthetase activity is expressed in a droplet, the second polynucleotide encoding the restriction endonuclease will also be transcribed and translated (1). This endonuclease can cleave a site outside the target gene on the polynucleotide fragment containing the target gene to generate a sticky end. The reaction is stopped and the droplets are disrupted. DNA fragments are recovered from the emulsion (2). A ligation step is required to ligate the adaptor to the cleaved DNA fragment (3). Adaptor-specific PCR is performed using the recovered DNA fragments (4). As a result, template DNA with adaptor ligated is preferentially amplified. The PCR product is used for the next round of selection or cloned.

Figure 2:
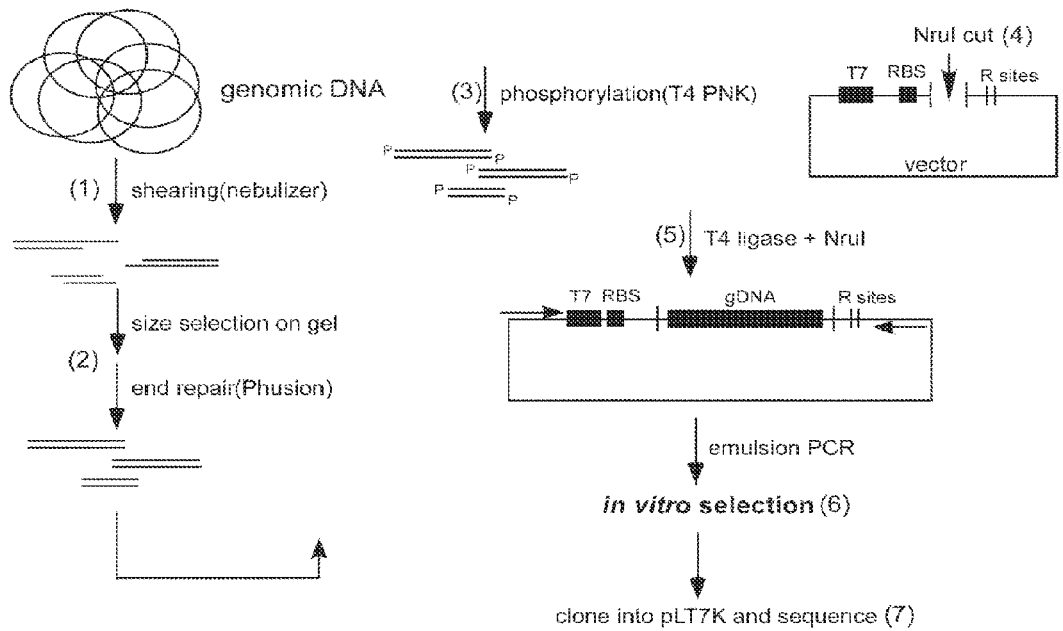

FIG. 2 provides a diagram of genomic library construction for in vitro selection of an enzyme. Genomic DNA is sheared using a nebulizer to create fragments having a size of less than 5 Kb (1) after which the DNA fragments are size-selected (1K-3K) on a gel and end-repaired using a Phusion™ polymerase (Finnzymes, Espoo, Finland) (2). The fragments are then phosphorylated with T4 polynucleotide kinase (3) and inserted into a pLT7K vector (Kong et al. *Nucleic Acid Res* 28:3216-3223 (2000)) (4) at a cloning site corresponding to an NruI cut site (5). A preparation of droplets is made where droplets contain a single vector and amplification reagents for performing emulsion PCR. The emulsion is then disrupted and the amplification products form the library of polynucleotides for selection and enrichment for a target gene (6). Accordingly, the library of polynucleotides are mixed with reagents for transcription and translation (PURE™ system, Genome Institute, Japan) and encapsulated in aqueous droplets in an emulsion. If a restriction endonuclease is encoded by the DNA fragment derived from the genome, then cleavage will occur and will be identified as described in FIG. 1A. If the gene to be cloned from the genome is a ligase, enrichment of the ligase gene will occur as described in 1B. In this way, an enzyme may be cloned from its natural hosts within as few as three rounds of selection (7).

FIGS. 3A-F show examples of enrichment of a target gene compared to a second template. Lane E shows the product of transcription and translation in the emulsion followed by ligation with an adaptor and PCR amplification. The amplification product is substantially enriched with respect to green fluorescent protein (GFP) when compared with the positive control.

Lane NC is a negative control that shows the product of amplification of the two genes in the absence of ligation and without use of an emulsion.

Lane PC is a positive control that shows the product of amplification of both genes in the presence of a restriction endonuclease and a ligase so that all fragments are ligated and amplified. As expected, GFP is overwhelmingly represented compared to PstI.

FIG. 3A shows a schematic of DNA templates used in the model libraries. The target gene is PstI-open reading frame-encoding PstI restriction endonuclease while the control is the gene encoding GFP. The PstI and genes differ in size.

FIG. 3B shows the results of a first cycle of amplification on a starting mixture of PstI and GFP in a ratio of 1:100. The lanes from left to right are E, NC, PC as explained above.

FIGS. 3C and D show the results of a first cycle and a second cycle of amplification, respectively, where the starting mixture contains PstI and GFP genes in a ratio of 1:1000. The lanes from left to right are E, NC, PC as explained above.

FIGS. 3E and F shows the results of a first cycle and second cycle of amplification, respectively, where the starting mixture contains PstI and GFP in a ratio of $1:10^4$ and $1:10^5$. The lanes from left to right are E and PC for each ratio. Residual amounts of GFP in E may result from the occasional presence of both genes in a single droplet where the restriction endonuclease produced by PstI gene acts on GFP also.

Note that in Lane E, the amount of the PstI gene is greatly enhanced.

FIGS. 4A-D show genomic selection of the PstI gene from Providencia stuartii.

FIG. 4A: 4Ai shows the starting genomic library. The smear between 1 kb and 3 kb contains amplified genomic templates generated in emulsions before enrichment. The single band in Lane 2 corresponds to empty plasmids.

4Aii and 4Aiii shows the result of amplification of the genomic library using a PstI gene-specific primer and a M.PstII-specific primer, respectively.

FIG. 4B: 4Bi shows the genomic library after a first round of gene selection and enrichment in E. NC is the total DNA from 4Ai.

4Bii shows enhanced amounts of the PstI gene after emulsion selection. Enrichment is not observed for M.PstII in 4Biii.

FIG. 4C: 4Ci shows the genomic library after a second round of gene selection and enrichment in E. NC corresponds to amplification of total DNA fragments resulting from break up of the emulsion after the first round of selection.

4Cii shows enhanced amounts of the PstI gene after emulsion selection. M.PstII gene is no longer detected using an M.PstI gene-specific primer (4Ciii).

FIG. 4D: 4Di shows the genomic library after a third round of gene selection and enrichment in E. NC corresponds to amplification of total DNA fragments resulting from break up of the emulsion after the second round of selection.

4Dii shows enhanced amounts of the PstI gene after emulsion selection. M.PstII gene is no longer detected using an M.PstI gene-specific primer (4Diii).

Figure 5:
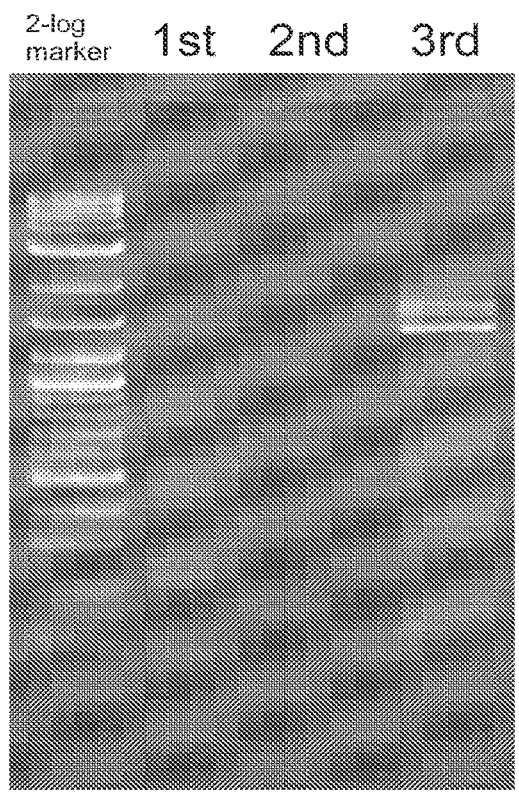

FIG. 5 shows genomic selection of the TspMI gene from *Thermus* sp. on a 1% agarose gel. Lanes 1st, $2^{nd}$ and 3rd show the adaptor-specific PCR amplification after each round of selection. Bands in the 3rd lane were cloned and confirmed to encode the TspMI gene.

Figure 6:
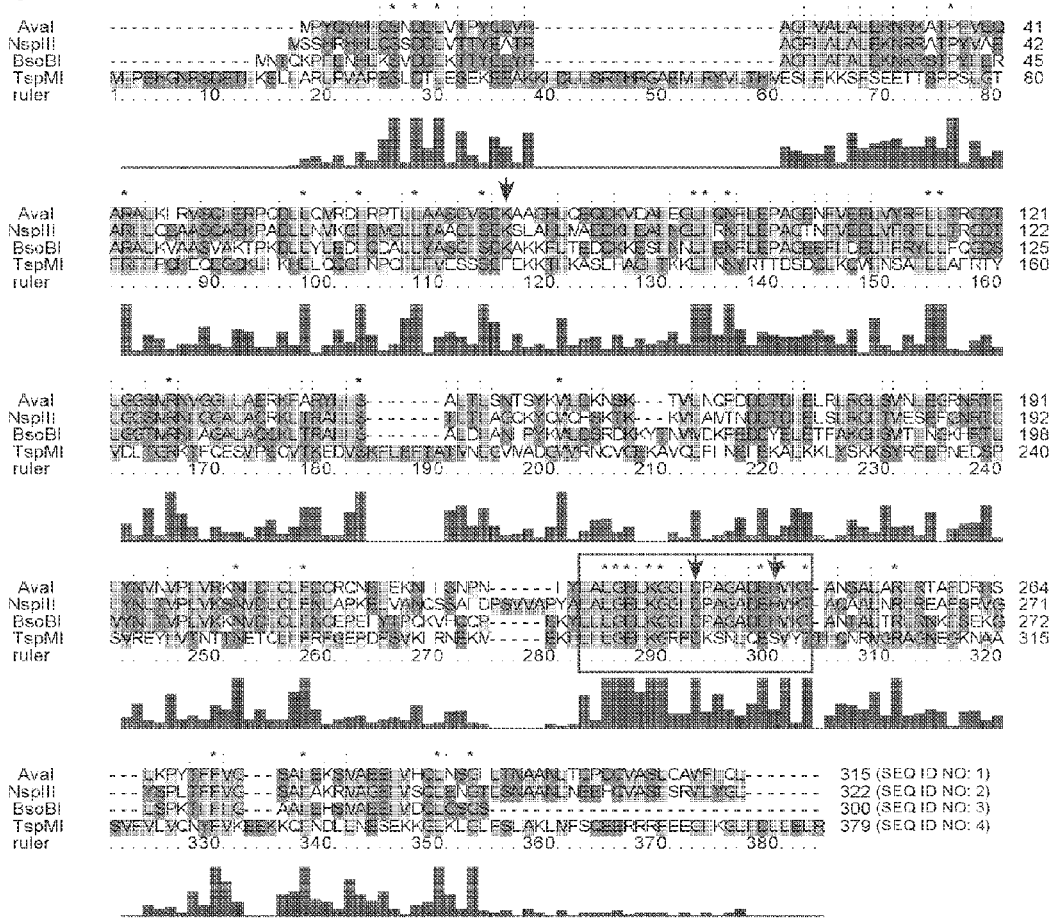

FIG. 6 shows the multiple alignment between AvaI (SEQ ID NO:1), NspIII (SEQ ID NO:2), BsoBI (SEQ ID NO:3) and the TspMI (SEQ ID NO:4) family. Predicted catalytic motifs (EXK) are shown in the box. The catalytic residue histidine is highlighted by the arrow between position 110 and 120.

TspMI is remotely similar to other protein sequences except the highly conserved region for catalysis. Arrows between positions 290 and 310 show the residues responsible for degenerate base recognition in the BsoBI family. The alignment was generated by ClustalW (Roberts *Proc Natl Acad Sci USA* 102:5905-5908 (2005)) and visualized by ClustaIX (Alves et al., *Nucleic Acids and Molecular Biology*, Pingoud, A. (ed.), Spring-Verlag: Berlin, Germany, Vol. 14, pp. 393-411 (2004)).

FIG. 7 shows the nucleotide sequence of TspMI (SEQ ID NO:5).

DETAILED DESCRIPTION OF THE EMBODIMENTS

In vitro compartmentalization offers a powerful method of directed evolution if selection and enrichment of the target gene can be optimized to allow efficient recovery from within the extensive sequence space. In embodiments of the invention, an approach to selection and enrichment has been developed that involves the ligation of adaptor molecules to polynucleotides from which target genes have been expressed and optionally modified. This approach provides as much as or greater than 100-fold enrichment during each round of selection and can be applied to a broad range of genes encoding selectable enzymatic activities.

In vitro compartmentalization relies on the formation of emulsions which may be produced from any suitable combination of immiscible liquids. Preferably, hydrophilic solvents form "aqueous" droplets of microscopic or colloidal size. "Droplets" are also referred to as "microcapsules" in the art. The aqueous droplets in the colloid can be formed from any hydrophilic material suitable for forming an emulsion, containing biochemical components in a stable form; and providing an environment in which the described reactions can occur. The hydrophobic liquid in which the droplets are suspended contains none of the reactants.

The emulsion may be stabilized by addition of one or more surface-active agents (surfactants). These surfactants are termed emulsifying agents and act at the hydrophilic/hydrophobic interface to prevent (or at least delay) separation of the phases. Many hydrophobic liquids such as oils and many emulsifiers can be used for the generation of biphasic emulsions; a recent compilation listed over 16,000 surfactants, many of which are used as emulsifying agents (Ash, M. and Ash, I. *Handbook of industrial surfactants*. Gower Publishing Ltd: Aldershot, Hampshire, UK (1993); and Schick, *Nonionic surfactants*. Marcel Dekker: N.Y. (1996)) such as sorbitan monooleate (SPAN® 80; ICI)) and polyoxyethylenesorbitan monooleate (TWEEN® 80; ICI)).

The use of anionic surfactants may also be beneficial. Suitable surfactants include sodium cholate and sodium taurocholate. Particularly preferred is sodium deoxycholate, preferably at a concentration of 0.5% w/v, or below. Addition of an anionic surfactant to the mixtures to be emulsified ensures that reactions proceed only after compartmentalization.

Creation of an emulsion generally requires the application of mechanical energy to force the phases together. There are a variety of ways of doing this that utilize a variety of mechanical devices, including stirrers (such as magnetic stir-bars, propeller and turbine stirrers, paddle devices and whisks), homogenizers (including rotor-stator homogenizers, high-pressure valve homogenizers and jet homogenizers), colloid mills, ultrasound and "membrane emulsification" devices (Becher, *Emulsions: theory and practice*. Reinhold: N.Y. (1957; Dickinson, *Emulsions and droplet size control*, pp. 191-257 Wedlock, D. J. (ed.), Butterworth-Heinemann: Oxford, U.K. (1994)).

The volume of the aqueous droplets is preferably of the order of between $5.2 \times 10^{-22}$ m$^3$ and $5.2 \times 10^{-16}$ m$^3$ corresponding to a sphere of diameter between 0.1 µm and 10 µm, more preferably between about $5.2 \times 10^{-19}$ m$^3$ and $6.5 \times 10^{-17}$ m$^3$ (1 µm and 5 µm), for example, 2-6 µm.

Aqueous droplets formed in emulsions are generally stable with little if any exchange of genetic elements or gene products between droplets. The technology exists to create emulsions with volumes all the way up to industrial scales of thousands of litres (Becher, *Emulsions: theory and practice*. Reinhold: N.Y. (1957); Sherman, *Emulsion science*. Academic Press: London, U.K. (1968); and Lissant, ed. "Emulsions and emulsion technology" in *Surfactant Science*, Marcel Dekker: N.Y. (1974 and 1984 editions).

A "polynucleotide fragment" refers to a double-stranded or single-stranded molecule or construct selected from the group consisting of a DNA molecule, an RNA molecule or a portion of RNA and a portion of DNA, a double strand hybrid consisting of a single-stranded RNA and a single-stranded DNA, or a partially or wholly artificial nucleic acid molecule consisting of exclusively synthetic or a mixture of naturally-occurring and synthetic bases. Any one of the foregoing may be linked to a polypeptide or other molecular group or construct at one end such that the other end is a sticky end or capable of conversion to a sticky end for ligating to an adaptor molecule. Advantageously, the "other" molecular group or construct may be selected from the group consisting of nucleic acids, polymeric substances, particularly beads, for example, polystyrene beads, magnetic substances such as magnetic beads, labels such as fluorophores or isotopic labels, chemical reagents, binding agents such as macrocycles and the like.

The polynucleotide fragment may include suitable regulatory sequences such as those required for efficient expression of the gene product, for example, promoters, enhancers, translational initiation sequences, polyadenylation sequences, splice sites and the like.

A "library of polynucleotide fragments" refers to a plurality of polynucleotide fragments having gene sequences that vary between individual polynucleotide fragments. Preferably one or more of the gene sequences encode a desired protein activity where these gene sequences are referred to as "the target gene". The target gene is capable of encoding a protein having a desired enzyme activity or binding activity where the activity is required for ligation of an adaptor to the end of the polynucleotide containing the target gene by means of sticky ends.

Methods of selection and enrichment are conducted for purposes of obtaining one or more target genes from the population of genetic elements in the polynucleotide fragments. Hence, it is assumed at the outset that the library of polynucleotide fragments contains one or more polynucleotide fragments containing gene sequences that encode a desired protein activity. In the absence of a target gene, selection and enrichment of the target gene cannot occur.

A "mixture of enzymes" refers to transcription and translation systems that involve multiple enzymes, the systems being commercially available (see for example, the NEB catalog, Ipswich, Mass.) and optionally additional reagent enzymes.

"Ligation" refers to covalent linkage of two polynucleotides. In embodiments of the method, ligation requires a polynucleotide fragment containing a target gene encoding a protein activity; a polynucleotide adaptor usually with sticky ends; and a protein with ligase activity if the protein with ligase activity is not encoded by the target gene. Additional components might optionally include a restriction endonuclease reagent or gene for cleaving a polynucleotide fragment to make a sticky end and/or a nicking endonuclease reagent or gene for use with a blunt end-cleaving restriction endonuclease. A restriction endonuclease is not always required for causing ligation as the polynucleotide library may be characterized in that all fragments have a sticky end but only those fragments encoding ligase activity will be selected for by adaptor-dependent selection.

In embodiments of the invention, ligation of adaptors is a prerequisite for selection and enrichment by IVC. Ligation may occur between the polynucleotide fragment and the adaptor if the target gene is expressed either because the target gene encodes a protein with ligase activity or endonuclease activity or the target gene must be expressed to permit a restriction endonuclease to create a sticky end on the polynucleotide fragment containing the target gene or the target gene has another activity that permits a ligase to join an adaptor to the polynucleotide by ligating sticky ends.

"Enhanced activity" is a term of art referring to an increase in an activity that can be selected for using embodiments of the method described herein.

"Sticky ends" refer to defined ends of double-stranded polynucleotide fragments in which there is a single stand overhang that is capable of covalently binding to a complementary single strand of a polynucleotide adaptor in the presence of a DNA or RNA ligase. "Sticky ends" may be generated on double-stranded RNA, double-stranded DNA or double-stranded RNA/DNA hybrids. The sticky ends may be formed by enzymatic cleavage by, for example but not limited to, a restriction endonuclease or may be formed by chemical synthesis.

"Amplification" refers to any primer-based replication of a DNA sequence known in the art. For example, amplification may be by the polymerase chain reaction (Saiki et al., *Science* 239:487-91 (1988)) or by using one of a variety of other gene amplification techniques including: Q beta replicase amplification (Cahill et al. *Clin. Chem.* 37:1482-5 (1991); Chetverin et al. *Progress Nucleic Acid Research Mol. Biol.* 51:225-70 (1995); and Katanaev et al. *Febs Lett* 359:89-92 (1995); the ligase chain reaction (LCR) (Landegren et al., *Science* 241: 1077-80 (1988); Barany *PCR Methods Applic.* 1:5-16 (1991); the self-sustained sequence replication system (Fahy et al., *PCR Methods Appl* 1:25-33 (1991), strand-displacement amplification (Walker et al., *Nucleic Acid Research* 20:1691-6 (1992), and helicase-dependent amplification (U.S. Pat. No. 7,282,328).

"A" is not intended to be limited to "one."

A library of polynucleotide fragments may express a protein from a target gene, which is selected from the library by its ability to become ligated to an adaptor, where the ligation event relies on expression of the target gene. The target gene can then be enriched by adaptor-specific amplification.

Figure 3:
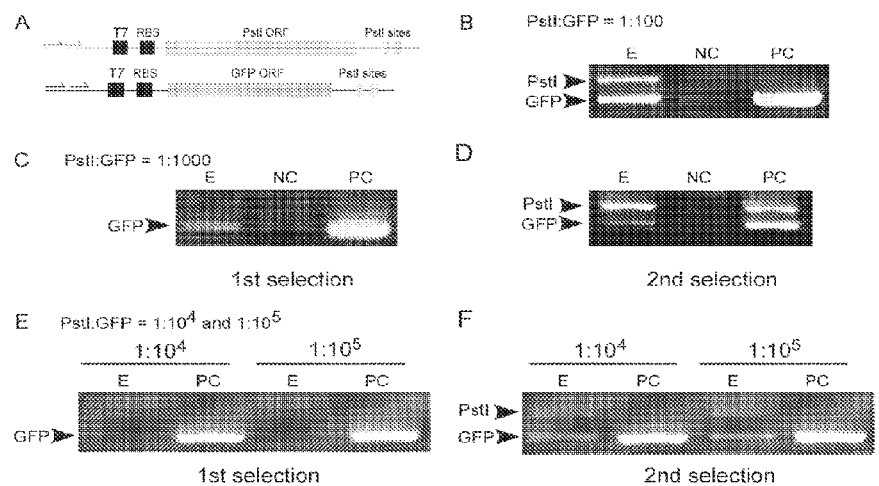

To determine the efficacy of embodiments of the method, the Example provided below describes how model selections were carried out using libraries of an excess of a GFP gene spiked with various amount of the gene encoding the PstI restriction endonuclease (recognition sequence CTGCA↓G) to generate a four-base 3'-overhang. After amplification, more than 50-fold enrichment was observed, more specifically, 100-fold enrichment in a single round of selection (FIG. 3). Multiple rounds of selection were carried out to achieve successive enrichment.

The enrichment of the target gene provided confidence that the embodiments were also suitable for selecting and enriching for novel genes from the genome of an organism. The Example below describes how the target gene encoding for PstI, a test restriction endonuclease that was already known, and a previously undescribed restriction endonuclease, TspMI, were selected and enriched from the genomes of the bacteria in which they occur (Providencia stuartii genome (PstI) and *Thermus* sp. (TspMI)). Libraries were constructed from the gDNA of a single bacterial species. In three rounds of iterative in vitro selections, the endonuclease gene became the single dominating DNA species in the resulting library. TspMI was subsequently cloned and sequenced for the first time.

Embodiments of the method provide an improved system for cloning restriction endonucleases which are known to be difficult to clone using standard techniques. The expressed restriction endonuclease encoded by a target gene in a polynucleotide fragment cleaves the polynucleotide at a specific site outside the putative gene. If the restriction endonuclease is expressed, a sticky end or a blunt end is created on the polynucleotide fragment. If the restriction endonuclease cleaves DNA to generate a blunt end, then an additional nicking endonuclease may be incorporated in the aqueous droplet and an appropriate recognition and nicking site may be introduced between the gene and the restriction endonuclease cleavage site in the polynucleotide fragment. In this way, a sticky end is created on the polynucleotide fragment after blunt end cleavage by the target gene product. A ligase may be added either to the aqueous droplet or to disrupted emulsion as a reagent to facilitate ligation between the adaptor which has a complementary sticky end to the polynucleotide and the polynucleotide fragment containing the target gene. Amplification is then carried out to provide a preparation of DNA in which the target gene has been enriched.

A restriction endonuclease may be involved in adaptor-dependent selection and enrichment not only for cloning a restriction endonuclease but also for selection and enrichment of a variety of other genes in several ways. These include:

(a) cleavage of the polynucleotide fragment to generate a sticky end prior to introducing the fragment into the IVC, for example, in selecting a protein with ligase activity and enriching a solution for that protein;

(b) cleaving a polynucleotide fragment before, during or after cleavage with a nicking endonuclease encoded by the polynucleotide fragment;

(c) as the expression product of the target gene;

as the expression product of a second polynucleotide fragment, for example, in selecting for a protein with transcription or translation enzyme activity such as tRNA synthetase activity; and/or enriching a solution for that protein; or (e) as a reagent enzyme contained in an aqueous particle, for example, in selecting for a protein with reverse transcriptase or ligase activity; and/or enriching a solution for that protein.

The observed selectivity and enrichment of target genes are applicable not just to restriction endonucleases but to a variety of other enzymes limited only by the experimental design that requires ligation of an adaptor to the polynucleotide fragment encoding the target gene. The use of adaptors allows for an efficient search for desired proteins in the vast sequence space.

Uses of embodiments of the method include the following:

(1) Selecting and enriching for mutants of restriction endonucleases. A library of DNA fragments can be generated in which each fragment contains a gene encoding an enzyme of interest and a restriction endonuclease cleavage sequence outside the mutated gene in the same DNA fragment.

Sources of the polynucleotide fragment may be a library of randomly mutagenized genes. Alternatively, the library may be a collection of different genes derived from an in vivo sample where, for example, the in vivo sample is a cell, an organism, or a population of different organisms, for example, micro-organisms from a soil sample.

In an embodiment of the invention, a library of polynucleotide fragments may be generated by, for example, the strategy described below for DNA. The gDNA of a single bacterial species is sheared into ORF-sized fragments (for example 1-3 Kb). The DNA fragments are then blunt-ended as required and ligated to known sequences at either end (for example a T7 promoter and a specific restriction endonuclease recognition/cleavage sequence plus additional sequence). The genomic fragments can then be amplified by emulsion PCR (Zheng et al. *Nucleic Acid Research* 35:e83 (2007)) to incorporate the restriction endonuclease recognition/cleavage sequence outside the gene. The amplified linear fragments are then incorporated into the IVC.

Individual DNA fragments are incorporated into droplets by in vitro compartmentalization, and any expressed restriction endonuclease that cleaves the DNA at the inserted cleavage site to generate defined sticky ends will be selected according to the ability of the DNA to ligate to an adaptor.

Addition of an adaptor ligated to these sticky ends results in selection of the desired genes. Only those templates that have been cleaved by the encoded endonuclease can be ligated efficiently. The adaptor-ligated templates are then amplified using adaptor-specific PCR to enrich for the target genes.

By three rounds of iterative in vitro selections using different adaptors for each round, the restriction endonuclease gene becomes the single dominating DNA species in the resulting library. Using this method, the PstI gene from Providencia stuartii and the TspMI gene from a *Thermus* species were cloned (see Example).

Because the ligation reaction is a key step in selection, the method may be modified for those endonucleases which generate shorter overhangs or blunt ends. In these circumstances, a recognition site of a nicking enzyme can be placed in proximity to the blunt end so that cleavage of the polynucleotide by the nicking enzyme results in a sticky end. Frequent cutters, such as those recognizing 4-base sites, sometimes fall outside of the application range since they tend to destroy their own genes. These enzymes are not toxic in living bacteria since a companion DNA methyltransferase protects the host. Nevertheless, it appears that the selective disadvantage of having self-destructing sites has driven a significant proportion of frequent cutters to lose the recognition sites within their genes. Table 1 lists the statistics of those restriction endonuclease genes having their own recognition sites within their genes. For example, for a gene of 1 kb in size, the probability that it does not have a particular 4-base site is approximately $e^{-4}$ (i.e., 0.018) according to the Poisson distribution. This sharply contrasts with the observation that over half of the 4-base recognizing restriction endonuclease genes do not have their own sites in their coding sequences (Table 1)

Once the polynucleotide fragment has been selected, the target gene can be cloned using standard cloning techniques. (Sambrook, et al. *Molecular cloning: a laboratory manual.* Cold Spring Harbor Laboratory Press New York (1989)). However, alternative techniques may be employed, as will be apparent to those skilled in the art. For example, the genetic information incorporated in the gene product may be incorporated into a suitable expression vector, and expressed therefrom.

(2) Selection and enrichment of mutants having reduced star activity compared to the wild-type enzymes. Instead of recognizing a single sequence for cleavage, restriction endonucleases with star activity cleave at various sites, which generally vary from each other by a single nucleotide. By designing adaptors to discriminate between different sticky ends, it is possible to select for modified enzymes with reduced star activity.

(3) Selection and enrichment of mutants of those native or recombinant restriction endonucleases that normally cleave outside the recognition site (for example, 20 nucleotides from the recognition site).

Selection and enrichment of mutants that cleave at an increased distance from the recognition site can be achieved by designing a DNA sequence with a predetermined number of nucleotides downstream of the recognition site that results in a target sticky end for ligating an adaptor.

(4) Selection and enrichment of a mutant restriction endonuclease that has nicking activity only may be achieved by, for example, allowing a mutant gene in a polynucleotide fragment to be expressed so as to nick at a site that is close to the end of the DNA fragment. As a result, a sticky end will be generated to which an adaptor can be ligated.

(5) Selection and enrichment of a ligase activity. Polynucleotide fragments may be digested by restriction endonucleases to generate defined ends. Adaptors and polynucleotide fragments are dispersed into in vitro compartments to allow in vitro transcription and translation. Adaptor-specific PCR may be used to amplify DNA fragments encoding ligase activity.

(6) Selection and enrichment of a gene encoding a protein having an enzyme activity involved in transcription and translation.

This may be achieved by incorporating one or more polynucleotide fragments from a library and a polynucleotide fragment that contains a gene for a restriction endonuclease together with a mixture of enzymes for transcription and translation into individual aqueous droplets in an emulsion absent a single transcription or translation protein encoded by the target gene. The library may be a genomic library or a library of mutagenized target genes. The selection process relies on the production of the protein encoded by the target gene by the transcription translation mixture in the absence of the protein encoded by the target gene. Subsequently, the polynucleotide encoding the restriction endonuclease can be transcribed and translated in a transcription and translation mix containing the protein encoded by the target gene. The protein with restriction endonuclease activity can then cleave the polynucleotide fragment from the library contained in the same droplet thereby producing a sticky end on the polynucleotide fragment for ligating to an adaptor either inside or outside the aqueous droplet. The target gene can then be amplified using adaptor-specific primers.

(7) Selection and enrichment for a mutagenized gene encoding a functional protein.

Emulsions can be used to efficiently screen for randomly mutagenized proteins having functionality. Traditional screening libraries of genes result in selection of mutants by various criteria. The mutants may be selected from a mixture in the library because of factors tangentially related to functionality such as translation efficiency, folding efficiency, preference for a particular buffer or catalytic efficiency. Many of these complicating factors can be avoided by using an emulsion selection and enrichment step. Individual genes are separated in discrete aqueous droplets in the presence of a transcription and translation system. The predominant criterion that determines the selection of a polynucleotide fragment is whether a protein is expressed and if so whether that protein has activity that results in a sticky end on the polynucleotide fragment and ligation of an adaptor to the polynucleotide fragment by means of the sticky ends.

Differentiation between different degrees of enzyme activity or specificity may be achieved within individual droplets or after amplification.

As described above, multiple rounds of selection can provide an increase in the recovery of variants possessing a desired property. Moreover, it has also been possible through multiple rounds of selection and enrichment using the embodiments described herein to elucidate specific nucleotides in a target gene which when mutated reveal a desired product, altered property or at least maintain functionality.

(8) Isolation of reverse transcriptase activity. The polynucleotide fragment can be a single strand RNA. If the RNA fragment contains a sequence encoding a reverse transcriptase, then in the presence of the required accessory factors such as RNA and DNA primers required for reverse transcription and complement strand synthesis in the aqueous droplet, double-stranded DNA will be formed. A restriction endonuclease is further included in the enzyme mixture for cleavage of the double-stranded product of reverse transcription thereby permitting ligation to an adaptor.

All references cited herein as well as U.S. provisional application Ser. No. 60/903,258 filed Feb. 23, 2007 are hereby incorporated by reference.

EXAMPLE

All PCRs were carried out using the high-fidelity Phusion™ polymerase (Finnzymes, Espoo, Finland) according to the manufacturer's instructions. All oligos were synthesized at New England Biolabs (NEB, Ipswich, Mass.) (see Table 3 for oligo details). DNA purifications, if not otherwise specified, used the spin-column procedure (Qiagen Inc., Valencia, Calif.). Enzymes, if not otherwise specified, are all from NEB, Ipswich, Mass.

Model Library Construction

The PstI gene was first cloned into the pLT7K vector (Kong et al., Nucleic Acids Res 28:3216-3223 (2000)) and then amplified from the plasmid. The GFP gene was amplified from the pIVEX-GFP vector (Roche, Basel, Switzerland). The 5'-untranslated regions upstream of the T7 promoter were the same for both templates. Both reverse primers had two tandem repeats of the PstI recognition site (CTGCAG) (FIG. 2A). PCR products were gel purified. The concentration of purified DNA was determined by A260 readings and by gel electrophoresis. Model libraries were constructed by mixing the PstI and GFP templates in variable molar ratios, 1:100, 1:103, 1:104 and 1:105, with a final concentration of 10 ng/µl.

Genomic Library Construction

Bacterial strains were obtained from the NEB (Ipswich, Mass.) strain collection. About 10 µg of purified gDNA was sheared using a nebulizer (Invitrogen, Carlsbad, Calif., K7025-05) according to the manufacturer's instructions. Sheared gDNA was precipitated by isopropanol, re-suspended in water and size-selected from 1 kb to 3 kb by agarose gel electrophoresis. The ends of size-selected gDNA were heterogeneous and were blunted using Phusion™ polymerase (3'→5' exo+) with dNTP at 72° C. for 2 hours (Finnzymes, Espoo, Finland). Purified blunt-ended gDNA fragments were phosphorylated using T4 polynucleotide kinase at 37° C. for 1 hour.

Vector pYZ6 was derived from pIVEX2.4 (Roche, Basel, Switzerland), with the following modifications: (1) the NruI site (TCG↓CGA) and the MscI site (TGG↓CCA) have been added to the multiple cloning region immediately after the ribosome-binding site to allow the insertion of blunt-ended DNA fragments; (2) two PstI sites were added after the multiple cloning region (two TspMI sites in the TspMI genomic selection). Circular pYZ6 plasmid was linearized by NruI digestion and purified. Ligation between the gDNA fragments and pYZ6 was carried out using T4 ligase in the presence of NruI (1 U/10 µl) at room temperature overnight. DNA was purified from the ligation mixture. 1 µl purified DNA was transformed into chemical competent cells (NEB, Ipswich, Mass., Turbo™) to judge the library quality and estimate the extent of coverage of the genome.

Emulsion PCR was then performed to "clonally" amplify linear DNA templates from the ligated gDNA using primers 561 and 825111 (Williams et al., Nat Methods 3:545-550 (2006)). 200 µl of the aqueous PCR mix was added to 400 µl stirring oil mix (4.5% v/v Span 80 (Fluka, Sigma-Aldrich, St. Louis, Mo.), 0.45% v/v Tween 80 (Sigma-Aldrich, St. Louis, Mo.), 0.05% Triton-X100 (EM BioSciences, San Diego, Calif.) in light mineral oil (Sigma-Aldrich, St. Louis, Mo.)) at 1000 rpm in a dropwise manner over 1.5 minutes. After the addition was completed, the stirring was continued for 5 minutes. The emulsion was pipetted into 10 aliquots of 50 µl in PCR tubes and overlaid with mineral oil. Reactions were heated to 98° C. for 60 s, then cycled 30 times (98° C. 10 s, 55° C. 20 s, 72° C. 90 s), then 7 min at 72° C. The primers for emulsion PCR annealed to the vector arms: the forward primer 561 was ~100 nt upstream of the T7 promoter and the reverse primer 825III was downstream of the PstI sites (see Table 3). Amplified DNA from emulsion PCR was purified as described in Williams et al. (Nat Methods 3:545-550 (2006)) (FIG. 4A) and used for in vitro selection.

Selection Using in vitro Compartmentalization

The reconstituted PURE™ system (Post Genome Institute, Japan) was used for in vitro transcription/translation reactions. 50 µl of chilled aqueous mix (25 µl solution A from PURE™ system, 10 µl solution B PURE™ system, 14 µl $H_2O$, 1 µl library) was added to 450 µl stirring oil mix (0.5% v/v Triton X-100 (EM Biosciences, San Diego, Calif.) and 4.5% v/v Span 80 (Fluka, Sigma-Aldrich, St. Louis, Mo.) in light mineral oil (Sigma-Aldrich, St. Louis, Mo.)) at 1200 rpm (Telesystem HP15P, Variomag, Daytona Beach, Fla.) and stirred for an additional 5 minutes. The emulsion was incubated at 37° C. for 2 hours to allow in vitro transcription/ translation. In PstI selections, the reactions in the emulsion were stopped by first heating to 80° C. for 20 minutes and then adding 50 µl quenching buffer (10 mM Tris, 20 mM EDTA, pH=8.0). The emulsion was then spun for 15 minutes at 14,000 rpm at 4° C. The upper oil phase was removed and the residual emulsion was broken by extracting with 1 ml water-saturated ether. Residual ether was removed by spinning for 5 minutes in a Speedvac. The DNA library was recovered by the spin-column procedure and eluted in 50 µl buffer EB (Qiagen, Valencia, Calif.).

Purified DNA after each emulsion selection was ligated with an excess (>100 fold) of short double-stranded adaptors (100-200 nt). Adaptors were excised from purified DNA by restriction enzyme digestions (see Table 3). 2 µl out of 10 µl ligation mix was used for adaptor-specific PCR (initial 98° C. 60 s, 30 cycles of 98° C. 10 s, 55° C. 20 s, 72° C. 60 s, final extension 72° C. 7 min). Forward primers used in successive rounds of selection were nested to increase the specificity of PCR. After PCR, DNA was spin-column purified and was used for the next round of selection.

Specific Enrichment of Restriction Endonuclease Genes

The selection of restriction endonuclease genes relies on their ability to generate sticky ends which are later used for ligation and PCR amplification, as illustrated in FIG. 1A. DNA templates for in vitro selection were engineered so that at one end there were the necessary elements for efficient transcription and translation (T7 promoter, ribosome binding site) and at the other end there were two tandemly repeated PstI recognition sites as the substrates (FIG. 3A). DNA templates mixed with the in vitro transcription/translation system were dispersed into up to $10^{10}$ aqueous droplets as artificial cells (Tawfik et al., Nat Biotechnol 16:652-656 (1998)). In droplets containing restriction endonuclease genes, active endonuclease were expressed in vitro and cleaved its own encoding DNA templates, leaving sticky ends at the tail. Active endonuclease molecules were confined to individual droplets to ensure the genotype-phenotype linkage. After the reaction in the emulsion was stopped, DNA templates were pooled and put into a ligation mixture with an excess of adaptors which have compatible sticky ends. Adaptor-specific PCR was then carried out to specifically amplify DNA templates to which the adaptor was ligated. This was achieved by using the reverse primer which only hybridizes to the adaptor while the forward primer was common to all DNA templates.

We constructed model libraries which consisted of two DNA templates, one had the PstI open reading frame (ORF) and the other had the GFP ORF. The two templates were mixed in variable molar ratios with decreasing concentration of the PstI template. The PstI template was about 1.3 kb in size and the GFP template was about 1.2 kb (FIG. 3A). Approximately $10^{10}$ (1 µl of model library at 10 ng/µl) template molecules were used when starting all model selections. The same amount was also used in the control experiments. As a positive control, the initial library was digested with pure PstI enzyme, followed by adaptor ligation and PCR amplification. We predicted that all templates in the library would be amplified in the positive control experiment and the final molar ratio between the templates would reflect the selection efficiency in the absence of a genotype-phenotype linkage. A negative control was carried out by directly putting the initial library into the ligation reaction followed by PCR amplification. Since DNA templates were blunt-ended PCR products, they would not ligate to adaptors with sticky ends and thus were not amplified. This was confirmed in FIG. 3 which showed a negative result in the negative control demonstrating no non-specific ligation or amplification.

Results from a single round of selection using a PstI: GFP=1:100 library are shown in FIG. 3B. In the positive control, GFP was preferentially amplified (FIG. 3B, lane PC) since it was the dominant species in the starting library, and in the negative control, almost no DNA was amplified (FIG. 3B, lane NC). In contrast, after emulsion selection, a bright band corresponding to the PstI template appeared with comparable intensity on top of the GFP band (FIGS. 3D and 3F, Lane E). Taken together, these experiments showed a specific enrichment of the PstI template. Similar results were observed in the first round of selection using the 1:1000 library (FIG. 3C). The final molar ratio between PstI and GFP after selection, as judged from the band intensities, was larger than 1:50 and was determined to be at least a 100-fold enrichment.

During an IVC selection, all templates that resided in the same droplet with a restriction endonuclease gene were amplified as "carryover". To eliminate the "carryover" templates, different adaptors were used between successive selections. FIGS. 3C and 3D show two rounds of selection using the 1:1000 library. After the first round, the PstI template was enriched by more than 100 fold (FIG. 3C, Lane E). The purified DNA after the first PCR was directly used in the next round of selection, after which the PstI template had become the dominant DNA species in the library (FIG. 3D, Lane E). Selections using the $1:10^4$ and $1:10^5$ libraries are shown in FIGS. 3E and 3F. After the first selection, very little DNA was amplified, (FIG. 3E, Lane E). After the second selection (FIG. 3F), bands corresponding to both PstI and GFP appeared on the gel with a ratio of approximately 1:1. A consistent 100-fold enrichment in each round of selection was observed.

Cloning DNA After Selection

DNA bands after selection were excised and purified on an agarose gel. Selected DNA was then digested with the restriction enzyme (PstI in PstI selection and XmaI in TspMI selection) and ligated into pLT7K. pLT7K was designed to accommodate toxic genes (Kong et al., Nucleic Acids Res 28:3216-3223 (2000)). Ligated DNA was transformed into NEB Turbo™ (Ipswich, Mass.) and plated onto LB-Amp plates. Plates were grown at 37° C. overnight. Individual clones were picked and grown in LB media with ampicillin. Plasmids were extracted by the mini-prep procedure and sequenced.

Genomic Selection of the PstI Gene

Having established that restriction endonuclease genes are effectively enriched from the model libraries, we continued to challenge the system with more complex libraries. A control experiment utilizing in vitro selection provided libraries constructed from a bacterial genome where we knew an active restriction endonuclease gene existed. The size of a typical bacterial genome varies from less than 1M bases to close to 10M bases. The size of a typical Type II restriction endonuclease gene is around 1 kb. The library complexity constructed from a bacterial gDNA was therefore calculated to be $10^5$. We selected the known PstI gene from its native host Providencia stuartii and later a new thermostable endonuclease TspMI gene from a Thermus sp.

A schematic diagram for the genomic library construction is shown in FIG. 2. Briefly, pure genomic DNA (gDNA) was sheared to less than 5 kb fragments using a nebulizer. Fragmented gDNA was then size-selected (1 k-3 k), blunt-ended and phosphorylated. The resulting gDNA fragments were ligated with the linearized vector which had the necessary elements for in vitro transcription/translation and selection. The ligated gDNA with the vector was then "clonally" amplified by using emulsion PCR (Williams et al., Nat Methods 3:545-550 (2006)). Amplified linear gDNA templates were used directly in the in vitro selection. The advantages of using emulsion PCR include reducing amplification bias and increasing the quality of the genomic library.

Figure 4:
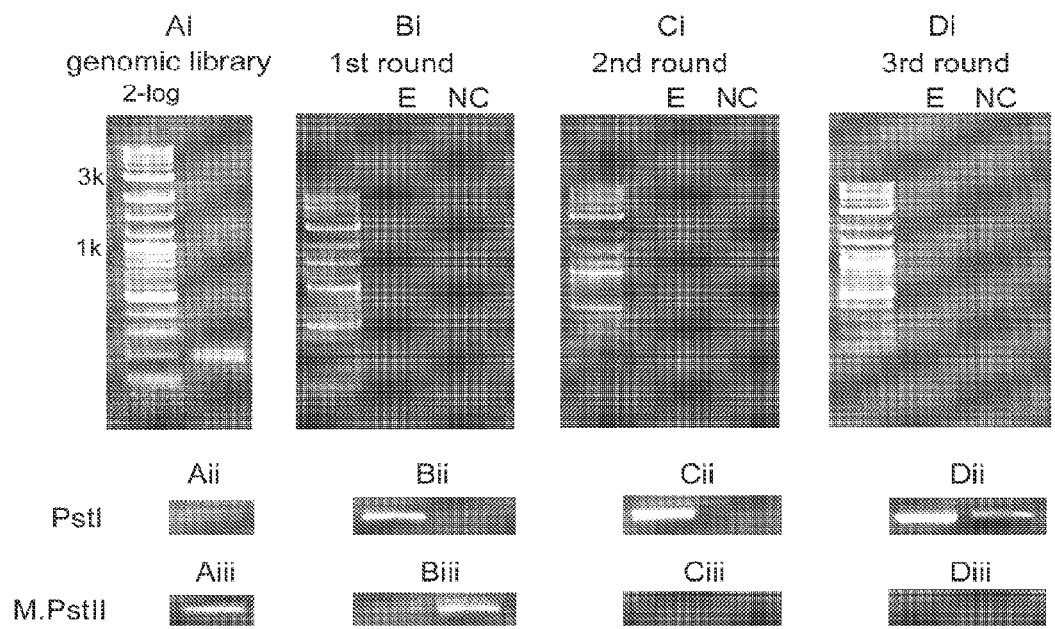

During the selection process, we monitored the presence of two reference genes in the libraries before and after selection by PCR: one was the target PstI gene and the other was a fragment from the DNA methyltransferase gene M.PstII (Sears et al., Nucleic Acids Res 33:4775-4787 (2005)), which does not possess endonuclease activity and is not located in the vicinity of the PstI gene on the chromosome. FIG. 4 shows the whole process of genomic selection. The starting genomic library is shown in FIGS. 4Ai-4Aiii, in which both PstI and the M.PstII fragment are present. Notice that the band intensities do not necessarily reflect their proportional abundance in the genomic library since there may be differences in individual PCR efficiencies.

The gel in FIG. 4Bi shows the results of the first adaptor-specific PCR for the emulsified genomic library and the negative control. There is no apparent difference between the two PCRs. However, individual PCR on the two reference genes suggests that the PstI gene was enriched in the emulsified library but not in the negative control. The control gene, M.PstII, was clearly not amplified (FIGS. 4Bii and 4Biii). The fact that less M.PstII is present in the emulsified library than in the negative control may be due to greater DNA sample loss in the emulsion selection. Lane E in FIG. 4Bi was purified and used for the next round of selection (FIG. 4(Ci)), after which only the desired PstI gene was present in the emulsified sample, and other contaminating genes, such as M.PstII, were diluted away (FIG. 4Ciii. Although it seems that only PstI-bearing templates survived the second selection, it was not enough to stand out on the gel. Lane E in FIG. 4Ci was purified and put into a third round of selection, after which a band of ~1.5 kb appeared in the emulsified library but not in the negative control (FIG. 4Di). Individual PCRs on the reference genes supported a consistent enrichment in the third round. It was later confirmed that this 1.5 kb band harbored the complete PstI genomic fragment. These results strongly suggest that enrichment of the PstI gene follows the expected course.

The ~1.5 kb band from the third selection was gel-purified, digested with PstI enzyme, and cloned into pLT7K for sequencing. The plasmid pLT7K was engineered to accommodate extremely toxic genes by combining controlled repression of the cloned gene and an anti-sense promoter to counter the lethal effects of basal expression (Kong et al., *Nucleic Acids Res* 28:3216-3223 (2000)). Sequenced inserts were compared with the fully sequenced PstI restriction-modification system (Roberts et al., *Nucleic Acids Res* 35:D269-270 (2007)) and results confirmed that there was one major product in the selected gDNA, which encompassed the full PstI ORF, with 3 nt upstream of the start codon and ~300 nt downstream of the stop codon. This result unambiguously showed that the selected DNA was indeed from the gDNA source and not from any possible contamination. Interestingly, the observation that all of the selected genomic fragments started 3 nt upstream of the PstI start codon indicated there might be selection pressure on the translation efficiency during genomic selections.

Genomic Selection of the TspMI Gene

We then applied the in vitro selection method to another thermostable endonuclease TspMI (recognition sequence C↓CCGGG) from *Thermus* sp. (Parashar et al., *Appl Microbiol Biotechnol* 72:917-923 (2006)), which had not been cloned before. TspMI is optimally active at 75-80° C. and retains about 20% activity at 37° C. (Roberts et al., *Nucleic Acids Res* 35:D269-270 (2007)). Based on these facts, in vitro selection differs slightly from the selection of PstI gene in that: (1) in the library construction, the ligation steps between the genomic fragments and the vector were performed in the presence of NruI and MscI enzymes individually to minimize the chance that either enzyme cuts inside the TspMI gene which would destroy the target gene to be selected; (2) the emulsion reaction was first incubated at 37° C. for in vitro transcription/translation and later moved to 65° C. briefly for efficient DNA cleavage; (3) since the TspMI enzyme cannot be deactivated by heat, only quenching buffer was used to stop the reaction and the process of DNA recovery was performed on ice. For comparison, traditional methylase selection (Szomolanyi et al., *Gene* 10:219-225 (1980)) was also performed to map the genomic region harboring the TspMI restriction-modification system.

FIG. 5 shows the adaptor-specific PCR after each round of selection using the library derived from the NruI ligation. As a result, multiple bands were observed after the third selection. These bands were digested by XmaI (recognition sequence C↓CCGGG), an isoschizomer of TspMI, and cloned into the vector, pLT7K. Sequenced clones with inserts contained an ORF of ~1.1 kb. This ORF coincided with the endonuclease gene acquired from the traditional methylase selection approach and later was confirmed to encode the active TspMI endonuclease gene. Analysis of five sequenced clones with genomic inserts suggested that the selected genomic fragments all started 36 nucleotides downstream from the predicted start codon and end at variable sites after the stop codon, leading to the pattern of multiple bands on the agarose gel. Selection using the library derived from MscI ligation yielded no bands. It was later found that there were multiple MscI sites inside the TspMI ORF so that the endonuclease gene had been destroyed during the ligation step. The sequence of the TspMI restriction-modification system is shown in FIG. 7.

The TspMI restriction-modification system is interesting in several ways. It contains the usual R and M genes as well as a nicking endonuclease gene (V gene) that is often found with m5C DNA methyltransferases. These endonucleases recognize the G-T mismatches that are formed following cytosine deamination, a spontaneous event that would be mutagenic if uncorrected. On the basis of sequence comparison, the TspMI gene appeared to be a member of a new family of genes recognizing CCCGGG, since it is quite dissimilar to the known families of genes represented by SmaI and XmaI (Table 2). In REBASE (Roberts et al., *Nucleic Acids Res* 35:D269-270 (2007)), there are 6 genes in the SmaI family and 7 in the XmaI family all of which are accompanied by DNA methyltransferases that form N4-methylcytosine. In the three known cases it is the second base in the recognition sequence that is modified. Given the sequence similarity among this set, it is likely they all modify this same base. In contrast, M.TspMI is an m5C methyltransferase showing only limited similarity to M.NmeAI (Cm5CGG).

The protein sequence of TspMI is only remotely similar to BsoBI (P-value>0.1), which is another thermostable restriction enzyme and recognizes C↓YCGRG (Y=C/T, R=A/G). This would be consistent with the relaxed specificity of BsoBI, which recognizes two sequences, CCCGAG and CTCGAG, as well as the specific sequence, CCCGGG, recognized by TspMI. Note that the relative position of cleavage within the recognition sequence is the same for both enzymes. FIG. 6 shows a multiple alignment of TspMI and BsoBI together with two other related enzymes, AvaI and NspIII that also recognize C↓YCGRG. Sequence conservation between TspMI and the BsoBI family is localized in the catalytic motif EXK (box of FIG. 6) (van der Woerd et al., *Structure* 9:133-144 (2001)). One interesting observation is that the conserved histidine residue in this region of the BsoBI family, which was suggested to act as a base to deprotonate a water molecule as a nucleophile (van der Woerd et al., *Structure* 9:133-144 (2001)), is replaced by a serine residue in TspMI. This suggests a slightly different catalytic mechanism possibly through serine-mediated nucleophilic attack. Two residues in BsoBI, Asp246 and Lys81 (see arrows in the box in FIG. 6), which were suggested to recognize degenerate base pairs and are conserved in the BsoBI family, have changed in TspMI, with aspartate conserved and lysine changed to phenylalanine. Again, this suggests a slightly different base recognition mechanism, possibly in accordance with the tightened specificity of TspMI.

TABLE 1

Statistics of restriction endonuclease genes having their own recognition sites within their coding sequences*

| Recognition site length | Total number | number of genes w/sites (percentage) | | | |
|---|---|---|---|---|---|
| | | 0 site | 1 site | 2 sites | more than 2 sites |
| 4 base | 117 | 64(55%) | 32(27%) | 14(12%) | 7(6%) |
| 5 base | 80 | 52(65%) | 19(23%) | 6(8%) | 3(4%) |
| 6 base | 157 | 138(88%) | 14(9%) | 4(3%) | 1(1%) |
| 7 base | 15 | 11(73%) | 4(23%) | 0 | 0 |
| 8 base | 10 | 10(100%) | 0 | 0 | 0 |

*All sequence data were retrieved from REBASE (Roberts et al., *Nucleic Acids Res* 35: D269-270 (2007)) as of February, 2007. Only experimentally verified restriction endonuclease genes are included in the analysis. Degenerate bases, "RYMKSW" (e.g., R = A or G) are counted as 0.5 base; while "BDHV" (e.g., B = C or G or T) are counted as 0.25 base.

TABLE 2

Sequence families of restriction enzymes that recognize CCCGGG

| Restriction Enzyme | Source | Methyltransferase |
|---|---|---|
| SmaI (CCC↓GGG) | *Serratia marcescens* Sb | C$^{m4}$CCGG |
| Cli245ORF1935P | *Chlorobium limicola* | unknown |
| CphBORF2531P | *Chlorobium phaeobacteroides* BS1 | unknown |
| CphORF2524P | *Chlorobium phaeobacteroides* | unknown |
| XcaVORF1110P | *Xanthomonas campestris* pv. *vesicatoria* str. 85-10 | unknown |
| XveIIP | *Xanthomonas campestris* pv. *vesicatoria* | unknown |
| XmaI (C↓CCGGG) | *Xanthomonas malvacearum* | unknown |
| Cfr9I | *Citrobacter freundii* | C$^{m4}$CCGG |
| Pac25I | *Pseudomonas alcaligenes* | unknown |
| XcyI | *Xanthomonas cyanopsidis* 13D5 | C$^{m4}$CCGG |
| MhuORF2537P | *Methanospirillum hungatei* JF-1 | unknown |
| StpORF334P | *Symbiobacterium thermophilum* | unknown |
| XaxGORFAP | *Xanthomonas axonopodis* pv. *glycines* plasmid AG1 | unknown |
| TspMI (C↓CCGGG) | Unidentified thermophile | $^{m5}$C |

The methyltransferases for the top two classes of restriction-modification systems are all closely related by sequence, suggesting they all modify the second cytosine residue in the recognition sequence to form N4-methylcytosine. In contrast, M.TspMI is an m5C methyltransferase showing limited similarity to M.NmeAI (Cm5CGG). Enzymes shown in bold have been characterized biochemically, the others are predicted on the basis of sequence similarity to XmaI or SmaI.

TABLE 3

Primers used in enrichment for target genes.

| | primers | sequence |
|---|---|---|
| Vector-specific primers* | 561 | GGTGATGCCGGCCACGATGCGTCC (SEQ ID NO: 6) |
| | 590 | GCGTAGAGGATCGAGATCTCGATCCCGCG (SEQ ID NO: 7) |
| | 625 | CGACTCACTATAGGGAGACCACAACG (SEQ ID NO: 8) |
| | 825III | TTCCGGATCTTAGTTAGTTACCGGATC (SEQ ID NO: 9) |
| Adaptor-specific primers** | Bamp | GTTGTAAAACGACGGCCAGTGAATTCGAGC (SEQ ID NO: 10) |
| | Samp | GCTTGCATGCCTGCAGGTCGACTCTAGA (SEQ ID NO: 11) |
| | BC4_4260 | GAACGGTCGTCAAGATTGATGGTCTGTGTGC (SEQ ID NO: 12) |
| | adaIII1 | GTAGTTCGCCAGTTAATAGTTTGC (SEQ ID NO: 13) |
| | 174_p1 | GCGCGCTTCGATAAAAATGATTGGCGTATC (SEQ ID NO: 14) |
| | pUC19_p1 | AGGAAACAGCTATGACCATGATTACGCCAA (SEQ ID NO: 15) |

*Vector-specific primers anneal to the pYZ6 plasmid. Primers 561, 590 and 625 anneal to upstream region of the T7 promoter. Primer 825III anneals to the downstream region of the cloning site. 590 was the nested primer of 561 and 625 was the nested primer of 590.
**Adaptor-specific primers -

For PstI selections, three adaptors were prepared: Adaptor I was gel-purified from a digestion of φX174 DNA with PstI and DraIII. The specific amplification primer was 174_p1. Adaptor II was gel-purified from the digestions of pUC19 DNA with PstI and SapI. The specific amplification primer was pUC19_p1. Adaptor III was gel-purified from the digestions of pBR322 DNA with PstI and BsaI. The specific amplification primer is adaIII1.

For TspMI selections, Adaptor I was gel-purified from the digestions of pUC19 DNA with XmaI and BglI. The specific amplification primer is Bamp. Adaptor II was gel-purified from the digestions of pUC19 DNA with XmaI and SapI. The specific amplification primer is Samp. Adaptor III was gel-purified from the digestions of pBC4 DNA with XmaI and BsaI. The specific amplification primer is BC4_4260. All DNA substrates and enzymes were from NEB, Ipswich, Mass.

What is claimed is:

1. An emulsion of a hydrophilic solution in a hydrophobic liquid, wherein the hydrophilic solution forms a plurality of droplets, each of the droplets containing:
   (i) a mixture of enzymes with transcription and translation activity;
   (ii) a polynucleotide adaptor with a sticky end; and
   (iii) a polynucleotide fragment from a library of polynucleotide fragments, wherein the polynucleotide fragment (a) has a sticky end or a recognition site for an enzyme capable of cleaving the polynucleotide to create a sticky end; and (b) encodes a protein selected from the group consisting of RNA ligase, DNA ligase, restriction endonuclease, nicking endonuclease, homing endonuclease, tRNA synthetase, RNA polymerase and reverse transcriptase, which if active, permits the adaptor to become ligated to the polynucleotide fragment.

2. The emulsion according to claim 1, further comprising (iv) one or more polynucleotide fragments not from the library, wherein the one or more polynucleotide fragments encodes a second protein.

3. The emulsion according to claim 2, wherein the second protein is a restriction endonuclease or a nicking endonuclease.

* * * * *

SEQUENCE LISTING

<160> NUMBER OF SEQ ID NOS: 15

<210> SEQ ID NO 1
<211> LENGTH: 315
<212> TYPE: PRT
<213> ORGANISM: Anabaena variabilis

<400> SEQUENCE: 1

Met Pro Tyr Gln Tyr His Ile Gln Ser Asn Asp Asp Leu Val Thr Pro
1               5                   10                  15

Tyr Gln Glu Val Arg Ala Gly Phe Val Ala Leu Ala Leu Glu Arg Asn
            20                  25                  30

Arg Lys Ala Thr Pro Phe Val Glu Gln Ala Arg Ala Leu Lys Ile Arg

-continued

```
            35                  40                  45
Val Ser Gln Ile Glu Arg Pro Gln Asp Leu Leu Gln Met Arg Asp Ile
 50                  55                  60

Arg Pro Thr Leu Leu Ala Ala Ser Gly Val Ser Asp Lys Ala Ala Gly
 65                  70                  75                  80

His Leu Gln Glu Gln Asp Lys Val Asp Ala Ile Glu Gly Leu Ile Gln
                 85                  90                  95

Asn Phe Leu Glu Pro Ala Gly Glu Asn Phe Val Glu Glu Leu Val Tyr
                100                 105                 110

Arg Phe Leu Leu Thr Arg Gly Asp Thr Leu Gly Gly Ser Met Arg Asn
                115                 120                 125

Val Gly Gly Ile Leu Ala Glu Arg Lys Phe Ala Arg Tyr Ile Ile Ser
130                 135                 140

Ala Leu Thr Leu Ser Asn Thr Ser Tyr Lys Trp Leu Asp Lys Asn Ser
145                 150                 155                 160

Lys Thr Trp Leu Asn Gln Pro Asp Asp Thr Asp Ile Glu Leu Arg
                165                 170                 175

Leu Arg Gly Leu Ser Trp Asn Leu Glu Gly Arg Asn Arg Thr Phe Ile
                180                 185                 190

Tyr Asn Val Asn Val Pro Ile Val Arg Lys Asn Ile Asp Ile Cys Leu
                195                 200                 205

Phe Asp Cys Arg Gln Asn Glu Ile Glu Lys Asn Ile Ile Ser Asn Pro
210                 215                 220

Asn Ile Tyr Ile Ala Leu Gly Glu Leu Lys Gly Gly Ile Asp Pro Ala
225                 230                 235                 240

Gly Ala Asp Glu His Trp Lys Thr Ala Asn Ser Ala Leu Ala Arg Ile
                245                 250                 255

Arg Thr Ala Phe Asp Arg His Ser Leu Lys Pro Tyr Thr Phe Phe Val
                260                 265                 270

Gly Ser Ala Ile Glu Lys Ser Met Ala Glu Glu Ile Trp His Gln Leu
                275                 280                 285

Asn Ser Gly Ile Leu Thr Asn Ala Ala Asn Leu Thr Gln Pro Asp Gln
290                 295                 300

Val Ala Ser Leu Cys Ala Trp Phe Ile Gln Leu
305                 310                 315

<210> SEQ ID NO 2
<211> LENGTH: 322
<212> TYPE: PRT
<213> ORGANISM: unknown
<220> FEATURE:
<223> OTHER INFORMATION: Nostoc species C

<400> SEQUENCE: 2

Met Ser Ser His Arg His His Leu Gln Ser Ser Asp Asp Leu Val Thr
 1               5                  10                  15

Thr Tyr Glu Ala Thr Arg Ala Gly Phe Ile Ala Leu Ala Leu Glu Lys
                 20                  25                  30

Asn Arg Arg Ala Thr Pro Tyr Val Ala Glu Ala Arg Ile Leu Gln Glu
                 35                  40                  45

Ala Ala Ser Gln Ala Glu Lys Pro Ala Asp Leu Leu Asn Val Lys Gly
 50                  55                  60

Ile Glu Met Gly Leu Leu Thr Ala Ala Gly Leu Ser Glu Lys Ser Leu
 65                  70                  75                  80

Ala His Leu Met Ala Glu Asp Lys Ile Glu Ala Ile Asn Gly Leu Ile
                 85                  90                  95
```

Arg Asn Phe Leu Glu Pro Ala Gly Thr Asn Phe Val Glu Glu Leu Val
                100                 105                 110

Phe Arg Phe Leu Leu Thr Arg Gly Asp Thr Leu Gly Gly Ser Met Arg
            115                 120                 125

Asn Ile Gly Gly Ala Leu Ala Gln Arg Lys Leu Thr Arg Ala Ile Leu
        130                 135                 140

Ser Thr Leu Thr Ile Ala Gly Gln Lys Tyr Gln Trp Gln His Ser Lys
145                 150                 155                 160

Thr Lys Lys Trp Ile Ala Met Thr Asn Asp Asp Thr Asp Ile Glu Leu
                165                 170                 175

Ser Leu Arg Gly Ile Thr Trp Glu Ser Glu Phe Gly Asn Arg Thr Leu
            180                 185                 190

Ile Tyr Asn Leu Thr Val Pro Leu Val Lys Ser Asn Val Asp Leu Cys
        195                 200                 205

Leu Phe Asn Leu Ala Pro Lys Glu Leu Val Ala Asn Gln Ser Ser Ala
210                 215                 220

Ile Asp Pro Ser Val Val Ala Pro Tyr Ala Ile Ala Leu Gly Glu Leu
225                 230                 235                 240

Lys Gly Gly Ile Asp Pro Ala Gly Ala Asp Glu His Trp Lys Thr Ala
                245                 250                 255

Gln Ala Ala Leu Asn Arg Ile Arg Glu Ala Phe Ser Arg Val Gly Tyr
            260                 265                 270

Ser Pro Leu Thr Phe Phe Val Gly Ser Ala Ile Ala Lys Arg Met Ala
        275                 280                 285

Gly Glu Ile Trp Ser Gln Leu Glu Asn Gly Thr Leu Ser Asn Ala Ala
290                 295                 300

Asn Leu Asn Glu Glu His Gln Val Ala Ser Ile Ser Arg Trp Leu Tyr
305                 310                 315                 320

Gly Leu

<210> SEQ ID NO 3
<211> LENGTH: 323
<212> TYPE: PRT
<213> ORGANISM: unknown
<220> FEATURE:
<223> OTHER INFORMATION: Bacillus stearothermophilus JN2091

<400> SEQUENCE: 3

Met Asn Thr Gln Lys Pro Phe Glu Asn His Leu Lys Ser Val Asp Asp
1               5                   10                  15

Leu Lys Thr Thr Tyr Glu Glu Tyr Arg Ala Gly Phe Ile Ala Phe Ala
            20                  25                  30

Leu Glu Lys Asn Lys Arg Ser Thr Pro Tyr Ile Glu Arg Ala Arg Ala
        35                  40                  45

Leu Lys Val Ala Ala Ser Val Ala Lys Thr Pro Lys Asp Leu Leu Tyr
    50                  55                  60

Leu Glu Asp Ile Gln Asp Ala Leu Leu Tyr Ala Ser Gly Ile Ser Asp
65                  70                  75                  80

Lys Ala Lys Lys Phe Leu Thr Glu Asp Lys Lys Glu Ser Ile Asn
                85                  90                  95

Asn Leu Ile Glu Asn Phe Leu Glu Pro Ala Gly Glu Glu Phe Ile Asp
                100                 105                 110

Glu Leu Ile Phe Arg Tyr Leu Leu Phe Gln Gly Asp Ser Leu Gly Gly
            115                 120                 125

Thr Met Arg Asn Ile Ala Gly Ala Leu Ala Gln Gln Lys Leu Thr Arg

-continued

```
            130                 135                 140
Ala Ile Ile Ser Ala Leu Asp Ile Ala Asn Ile Pro Tyr Lys Trp Leu
145                 150                 155                 160

Asp Ser Arg Asp Lys Lys Tyr Thr Asn Trp Met Asp Lys Pro Glu Asp
                165                 170                 175

Asp Tyr Glu Leu Glu Thr Phe Ala Lys Gly Ile Ser Trp Thr Ile Asn
            180                 185                 190

Gly Lys His Arg Thr Leu Met Tyr Asn Ile Thr Val Pro Leu Val Lys
                195                 200                 205

Lys Asn Val Asp Ile Cys Leu Phe Asn Cys Glu Pro Glu Ile Tyr Thr
210                 215                 220

Pro Gln Lys Val His Gln Gln Pro Glu Lys Tyr Leu Leu Gly Glu
225                 230                 235                 240

Leu Lys Gly Gly Ile Asp Pro Ala Gly Ala Asp Glu His Trp Lys Thr
                245                 250                 255

Ala Asn Thr Ala Leu Thr Arg Ile Arg Asn Lys Phe Ser Glu Lys Gly
                260                 265                 270

Leu Ser Pro Lys Thr Ile Phe Ile Gly Ala Ala Ile Glu His Ser Met
275                 280                 285

Ala Glu Glu Ile Trp Asp Gln Leu Gln Ser Gly Ser Leu Thr Asn Ser
290                 295                 300

Ala Asn Leu Thr Lys Thr Glu Gln Val Gly Ser Leu Cys Arg Trp Ile
305                 310                 315                 320

Ile Asn Ile
```

<210> SEQ ID NO 4
<211> LENGTH: 379
<212> TYPE: PRT
<213> ORGANISM: unknown
<220> FEATURE:
<223> OTHER INFORMATION: Unidentified thermophile

<400> SEQUENCE: 4

```
Met Ile Pro Glu His Gly Asn Arg Ser Asp Glu Thr Ile Lys Glu Leu
1               5                   10                  15

Ile Ala Arg Leu Pro Trp Ala Pro Glu Ser Leu Asp Thr Leu Glu Ser
                20                  25                  30

Glu Lys Glu Glu Ala Lys Lys Ile Asp Leu Leu Ser Arg Thr His Arg
            35                  40                  45

Gly Ala Glu Met Ile Arg Tyr Val Leu Thr His Met Glu Ser Ile Phe
        50                  55                  60

Lys Lys Ser Phe Ser Glu Glu Thr Thr Ser Pro Pro Ser Leu Gly Thr
65                  70                  75                  80

Phe Arg Phe Phe Pro Gln His Glu Gln Glu Gly Gln Lys Leu Ile Lys
                85                  90                  95

His Leu Leu Gln Gln Gly Ile Asn Pro Gln Ile Leu Phe Val Glu Ser
            100                 105                 110

Ser Ser Asp Phe Glu Lys Lys Thr Ile Lys Ala Ser Leu His Ala Gly
        115                 120                 125

Ile Thr Lys Lys Leu Ile Asn Asn Tyr Arg Thr Thr Asp Ser Asp Gln
    130                 135                 140

Leu Lys Gln Trp Ile Asn Ser Ala Ile Leu Leu Ala Phe Arg Thr Tyr
145                 150                 155                 160

Val Asp Leu Thr Gly Arg Lys Thr Phe Gln Glu Ser Trp Pro Glu Cys
                165                 170                 175
```

```
Val Thr Lys Glu Asp Val Ser Lys Phe Leu Glu Phe Thr Ala Thr Met
            180                 185                 190
Asn Leu Gly Val Met Ala Asp Gly Trp Trp Arg Asn Gln Val Gly Glu
        195                 200                 205
Lys Ala Val Gln Leu Phe Ile Asn Glu Ile Glu Lys Ala Leu Lys Lys
210                 215                 220
Leu Tyr Ser Lys Lys Ser Tyr Arg Phe Glu Pro Asn Glu Asp Ser Pro
225                 230                 235                 240
Ser Val Arg Glu Tyr Ile Val Thr Asn Thr Thr Asn Glu Thr Gln Leu
                245                 250                 255
Ile Phe Arg Phe Gly Glu Pro Asp Phe Ser Val Lys Ile Arg Asn Glu
            260                 265                 270
Lys Met Glu Lys Ile Leu Ile Leu Gly Glu Ile Lys Gly Arg Phe Asp
        275                 280                 285
Lys Ser Asn Leu Gln Glu Ser Trp Tyr Thr Thr Ile Gln Asn Arg Met
290                 295                 300
Gly Arg Ala Gly Asn Glu Gly Lys Asn Ala Ala Ser Val Phe Val Leu
305                 310                 315                 320
Val Gln Asn Tyr Phe Val Lys Glu Lys Lys Gln Ile Asn Asp Leu
                325                 330                 335
Leu Asn Glu Ser Glu Lys Lys Gly Leu Lys Leu Gly Leu Phe Ser Leu
            340                 345                 350
Ala Lys Leu Met Phe Ser Gln Glu Glu Arg Arg Phe Glu Glu Cys
        355                 360                 365
Ile Lys Gly Leu Ile Asp Leu Leu Glu Leu Arg
        370                 375

<210> SEQ ID NO 5
<211> LENGTH: 3271
<212> TYPE: DNA
<213> ORGANISM: unknown
<220> FEATURE:
<223> OTHER INFORMATION: unidentified thermophile

<400> SEQUENCE: 5
gcgcctggcg gagctggtga gggaggaggc gggggacctt caggaggctc cgcccccag        60 ggaggagagg cccggggagg cccctcacgg ggggggcctc gagggctccc cgccgggcga      120
gggccaagcg gagcgccccc tccccccta cctcacctac gtccgcaagg agtgccgcct       180 ccgcccccgac cagctggacg ccctcaccgc cctggccggg agaggaaggg gaaggggaa      240 aggatcacgg agaacaccct catccgctgg gcggtggact acttttgaa aaaactagag      300 ctggaaacgg ggagcgacgg aaaggaggtg acatgacgcg gatgttcgag acgcttgcag      360
aacttgagca cgcttttcaa aacttgcgcg aacaacttgg cgcaatggta acggcgaatg      420
aagactttcc cctttggtc gtcgaccttt tttccggagc cggcggcatg tcctacggct       480
tcaaatattg gggggatagg ctttacaaaa taatcggtgc ggtggatctc gaggtggcca      540
aacccagcga cagcaaggca aaaaagggcg gcggggaac gaactgcaac gccacatacg      600
aggccaatat cggcatacgc ccgttaaaag ccgatataac ggaacttaat ccccgtgaat      660
acagagaaaa tttgggtctt gaagtgggtc agttaggcgt acttatttcc tgcgccccct      720
gcacgggatt cagtcaaaaa aactttctga accaccagaa cgatgaccca cgaaaccact      780
tggtgaggag aagcgggggtt ttttggagg aattttttacc agagttcttc gtgatggaaa    840
acgtcccaga aatgatgttg ggaaaacacc gtcaccattt tgaagaactg aaggagatac      900
tcgtaggttt gggttattcc tacaccgccg gcgtgttgga tttctccact ctaggttttgc    960
```

```
cgcaacgaag aaagcgtgcc gtggttatgg cctggcggga aggtagacga atcccggctc    1020
tacctcgctt tttctcttcc cctcctacgg tacgggaggc aatcggccat cttccacctc    1080
tctccgccgg agaaacacat ccaaacgatc cgatgcacag atgtccaagg cacaccccgg    1140
aggtcatgga aagaattaag gccgtaccca gggacggagg ttcctggatc gacttggcct    1200
ccagaaatcc ggaactcctt attccctcga tgaaaaggaa actacgggaa ggaaagaagg    1260
ggtcttttcc cgacgtctac ggacggatgt cctggaattc ccccgcgcct acgatcacga    1320
gggaatgcgg ccaccccggc aacgacgct acctacaccc cgaacaggac aggatgttat     1380
ctataaggga gatggctata ttacaaggtt ttcctcccaa ttcacccttt attggaaacc    1440
tcaaccaatg ctacaaccaa atcggagacg cggttccccc cctggtttct cgcacgattg    1500
cgggcctctt tctcctcctg aagctcgggc tgaactgggg ccaagtcatg aaccgccata    1560
tacatgtctc caatctcaat tggctttatt tcgaagagca cgtcccgaga gcgcaggtgg    1620
aacaggatcc tctcctaata ccctaagccg gttgccgtac atctagagga ggaaaacgat    1680
gatcccggaa cacggaaaca gaagcgacga acaatcaag gaattaatcg cccgccttcc     1740
ctgggcaccc gaaagcttgg atacgctaga gagcgagaaa aagaagcaa aaaaaatcga     1800 tttgctttcg agaacacata gaggtgcgga aatgatacgt tacgttctaa cacacatgga    1860
gtccatcttc aaaaaatcgt tctctgagga gactacctcc ccccctagcc tcggcacttt    1920
ccgcttcttt cctcagcatg aacaagaagg ccaaaagctt ataaagcatc ttttacaaca    1980
aggcataaac ccgcaaattc ttttcgtaga aagtagttcc gattttgaga aaaaacaat    2040 aaaagcaagt ttacacgcag gcataaccaa aaaactcatc aacaactacc gcacgacgga    2100
cagcgatcag ctcaaacagt ggatcaactc ggcaatactc ctcgccttcc ggacctacgt    2160
tgatttgact gggaggaaaa ccttccaaga aagctggcca gagtgcgtaa ccaaagaaga    2220
cgtctcaaaa ttcttggagt ttaccgcaac gatgaacttg ggagtcatgg cggacggctg    2280
gtggagaaac caggtaggtg agaaagctgt gcaacttttc ataaatgaaa tcgagaaggc    2340
gttgaagaag ctttattcaa aaaaatccta tcgttttgag cctaacgagg acagcccgag    2400
cgtccgcgaa tacatcgtaa ccaacaccac caacgaaacg caactgattt ttcgattcgg    2460
agaaccagat ttttctgtaa aaatccgcaa cgaaaaaatg gaaaaaatac tcattttagg    2520
cgaaataaag gggcgctttg acaaatcgaa cctacaagag agctggtaca caaccatcca    2580
aaataggatg ggaagggcag gaaacgaggg caaaaacgcg gccagtgttt ttgttcttgt    2640
tcaaaattac tttgtgaagg aagaaaagaa acaaataaat gatcttttga acgaaagtga    2700
aaaaaagggc ctcaagttgg gtcttttcag cttggccaag ttgatgttct ctcaagagga    2760
gaggcgaaga tttgaagaat gcatcaaagg cctgatcgac cttctagagc tccgataacc    2820
ctggcaacag cttcctgcgg cgccttttc aattcatgtt cccaaatcct tacgaccgac     2880 caccccctgtc tggccaggag ttcatcaact cgtgcatcgc gttgcctgtt ctcttttatc   2940
ttcctcctcc aaaactccgc attcgtctta ggtttcttat tacagacggg gcaaccgtgc    3000
cagaaacatc cgtcgacaaa aatcgccact ttccgtttgg gaaatacgac atccggtcgc    3060
ccaggaaggt tgttttttat acggtagccc cttataccgg caacccgcaa gagacgacgc    3120
aactttactt ccggtcccgt ggaggaagtc tttactttcc tcatcaactc agatcttttc    3180
tccggagtaa aaatatccat aaaaaccccg tgtcgaaatc ggctcggctt aatcctagac    3240
aagcacttcc ggcagcgccc gggcggcctc c                                   3271
```

-continued

```
<210> SEQ ID NO 6
<211> LENGTH: 24
<212> TYPE: DNA
<213> ORGANISM: unknown
<220> FEATURE:
<223> OTHER INFORMATION: vector-specific primer

<400> SEQUENCE: 6
ggtgatgccg gccacgatgc gtcc                                          24

<210> SEQ ID NO 7
<211> LENGTH: 29
<212> TYPE: DNA
<213> ORGANISM: unknown
<220> FEATURE:
<223> OTHER INFORMATION: vector-specific primer

<400> SEQUENCE: 7
gcgtagagga tcgagatctc gatcccgcg                                     29

<210> SEQ ID NO 8
<211> LENGTH: 26
<212> TYPE: DNA
<213> ORGANISM: unknown
<220> FEATURE:
<223> OTHER INFORMATION: vector-specific primer

<400> SEQUENCE: 8
cgactcacta tagggagacc acaacg                                        26

<210> SEQ ID NO 9
<211> LENGTH: 27
<212> TYPE: DNA
<213> ORGANISM: unknown
<220> FEATURE:
<223> OTHER INFORMATION: vector-specific primer

<400> SEQUENCE: 9
ttccggatct tagttagtta ccggatc                                       27

<210> SEQ ID NO 10
<211> LENGTH: 30
<212> TYPE: DNA
<213> ORGANISM: unknown
<220> FEATURE:
<223> OTHER INFORMATION: adaptor-specific primer

<400> SEQUENCE: 10
gttgtaaaac gacggccagt gaattcgagc                                    30

<210> SEQ ID NO 11
<211> LENGTH: 28
<212> TYPE: DNA
<213> ORGANISM: unknown
<220> FEATURE:
<223> OTHER INFORMATION: adaptor-specific primer

<400> SEQUENCE: 11
gcttgcatgc ctgcaggtcg actctaga                                      28

<210> SEQ ID NO 12
<211> LENGTH: 31
<212> TYPE: DNA
<213> ORGANISM: unknown
<220> FEATURE:
<223> OTHER INFORMATION: adaptor-specific primer

<400> SEQUENCE: 12
```

-continued

```
gaacggtcgt caagattgat ggtctgtgtg c                              31

<210> SEQ ID NO 13
<211> LENGTH: 24
<212> TYPE: DNA
<213> ORGANISM: unknown
<220> FEATURE:
<223> OTHER INFORMATION: adaptor-specific primer

<400> SEQUENCE: 13
gtagttcgcc agttaatagt ttgc                                      24

<210> SEQ ID NO 14
<211> LENGTH: 30
<212> TYPE: DNA
<213> ORGANISM: unknown
<220> FEATURE:
<223> OTHER INFORMATION: adaptor-specific primer

<400> SEQUENCE: 14
gcgcgcttcg ataaaaatga ttggcgtatc                                30

<210> SEQ ID NO 15
<211> LENGTH: 30
<212> TYPE: DNA
<213> ORGANISM: unknown
<220> FEATURE:
<223> OTHER INFORMATION: adaptor-specific primer

<400> SEQUENCE: 15
aggaaacagc tatgaccatg attacgccaa                                30
```